United States Patent
San et al.

(10) Patent No.: US 10,011,854 B2
(45) Date of Patent: Jul. 3, 2018

(54) FATTY ACID PRODUCTIVITY

(71) Applicant: WILLIAM MARSH RICE UNIVERSITY, Houston, TX (US)

(72) Inventors: Ka-Yiu San, Houston, TX (US); Wei Li, Houston, TX (US)

(73) Assignee: William Marsh Rice University, Houston, TX (US)

(*) Notice: Subject to any disclaimer, the term of this patent is extended or adjusted under 35 U.S.C. 154(b) by 0 days.

(21) Appl. No.: 15/095,158

(22) Filed: Apr. 11, 2016

(65) Prior Publication Data

US 2016/0215309 A1 Jul. 28, 2016

Related U.S. Application Data

(63) Continuation-in-part of application No. PCT/US2014/059319, filed on Oct. 6, 2014.

(60) Provisional application No. 61/889,166, filed on Oct. 10, 2013.

(51) Int. Cl.
| | |
|---|---|
| C12N 1/20 | (2006.01) |
| C12P 7/64 | (2006.01) |
| C12P 7/62 | (2006.01) |
| C12N 9/00 | (2006.01) |
| C12N 9/02 | (2006.01) |
| C07H 21/04 | (2006.01) |
| C12N 9/04 | (2006.01) |
| C12N 9/16 | (2006.01) |

(52) U.S. Cl.
CPC .......... *C12P 7/6409* (2013.01); *C12N 9/0006* (2013.01); *C12N 9/16* (2013.01); *C12Y 101/011* (2013.01); *C12Y 101/0133* (2015.07); *C12Y 301/02014* (2013.01); *C12Y 101/01* (2013.01)

(58) Field of Classification Search
None
See application file for complete search history.

(56) References Cited

U.S. PATENT DOCUMENTS

| | | | |
|---|---|---|---|
| 2013/0040340 A1* | 2/2013 | Dauner | C12P 7/6436 435/42 |
| 2014/0004580 A1* | 1/2014 | Roberts | C12N 9/0008 435/134 |
| 2014/0093921 A1 | 4/2014 | San et al. | |
| 2014/0193867 A1 | 7/2014 | San et al. | |
| 2014/0212935 A1 | 7/2014 | San et al. | |

FOREIGN PATENT DOCUMENTS

| | | | |
|---|---|---|---|
| WO | WO2010142522 | | 12/2010 |
| WO | WO2011064183 | | 6/2011 |
| WO | WO 2011-116279 | * | 9/2011 |
| WO | WO2011116279 | | 9/2011 |
| WO | WO2012052468 | | 4/2012 |
| WO | WO 2012-087963 | * | 6/2012 |
| WO | WO 2012-109221 | * | 8/2012 |
| WO | WO2013059218 | | 4/2013 |
| WO | WO2013096665 | | 6/2013 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Kisselev L., Polypeptide release factors in prokaryotes and eukaryotes: same function, different structure. Structure, 2002, vol. 10: 8-9.*
Gurvitz Aner, The essential mycobacterial genes, fabG1 and fabG4, encode 3-oxoacyl-thioester reductases that are functional in yeast mitochondrial fatty acid synthase type 2, Mol Genet Genomics (2009), 282: 407-416.*
Bergler H, et a., Protein EnvM is the NADH-dependent enoyl-ACP reductase (FabI) of *Escherichia coli*, J Biol Chem. 269(8):5493-6 (1994).
Bokinsky G. et al., Synthesis of three advanced biofuels from ionic liquid-pretreated switchgrass using engineered *Escherichia coli*, PNAS, 108(50): 19949-19954 (2011).
Caughey I, Kekwick RG, The characteristics of some components of the fatty acid synthetase system in the plastids fom the mesocarp of avocado (*Persea americana*) fruit, Eur J Biochem. 123(3):553-61 (1982).
Dutta D, et al., Crystal structure of FabG4 from *Mycobacterium tuberculosis* reveals the importance of C-terminal residues in ketoreductase activity, J Struct Biol. 174(1):147-55 (2011).
Fuhrer T, Sauer U. Different biochemical mechanisms ensure network-wide balancing of reducing equivalents in microbial metabolism, J Bacteriol. 191(7):2112-21 (2009).
Jing et al., Phylogenetic and experimental characterization of an acyl-ACP thioesterase family reveals significant diversity in enzymatic specificity and activity, BMC Biochemistry 2011, 12:44.
Martinez I, et al., Replacing *Escherichia coli* NAD-dependent glyceraldehyde 3-phosphate dehydrogenase (GAPDH) with a NADP-dependent enzyme from Clostridium acetobutylicum facilitates NADPH dependent pathways, Metab Eng. 10(6):352-9 (2008).
Murarka A., et al., Fermentative Utilization of Glycerol by *Escherichia coli* and Its Implications for the Production of Fuels and Chemicals, Appl Environ Microbiol. Feb. 2008; 74(4): 1124-1135.
Radakovits, R., Eduafo, P.M. and Posewitz, M.C. Genetic engineering of fatty acid chain length in Phaeodactylum tricornutum. Metab. Engin., 13, 89-95 (2011).

(Continued)

*Primary Examiner* — Iqbal H Chowdhury
(74) *Attorney, Agent, or Firm* — Boulware & Valoir

(57) ABSTRACT

The present disclosure relates to an engineered microbe capable of improved productivity of fatty acid or fatty acid derivative. An $NAD^+$-dependent 3-oxoacyl-ACP reductase or $NAD^+$-dependent 3-oxoacyl-CoA reductase replaces or supplements the native $NADP^+$-dependent 3-oxoacyl-ACP reductase so as to utilize the higher availability of $NAD^+$ rather than $NADP^+$ in the cell. Higher production, yield and titer of fatty acids are therefore obtained. Such microbes can be combined with other mutations to further improve yield of fatty acids or fatty acid derivatives.

7 Claims, 17 Drawing Sheets

(56) References Cited

OTHER PUBLICATIONS

Ruffing, A.M. & Jones, H.D.T. Physiological effects of free fatty acid production in genetically engineered Synechococcus elongatus PCC 7942. Biotechnology and Bioengineering, 2012; 109 (9): 2190.
Sanchez AM, et al., Effect of overexpression of a soluble pyridine nucleotide transhydrogenase (UdhA) on the production of poly(3-hydroxybutyrate) in *Escherichia coli*, Biotechnol Prog. 22(2):420-5 (2006).
Wang Y, at al, Improvement of NADPH bioavailability in *Escherichia coli* by replacing NAD+-dependent glyceraldehyde-3-phosphate dehydrogenase GapA with NADP +-dependent GapB from Bacillus subtilis and addition of NAD kinase, J Ind Microbiol Biotechnol. 2013. PMID: 24048943.
Zhang X, Li M, Agrawal A, San KY, Efficient free fatty acid production in *Escherichia coli* using plant acyl-ACP thioesterases, Metab Eng. 13(6):713-22 (2011).

* cited by examiner

FIGURE 1C

| Step | Enzyme | Reaction | Description |
|---|---|---|---|
| (a) | Acetyl CoA:ACP transacylase | | Activates acetyl CoA for reaction with malonyl-ACP |
| (b) | Malonyl CoA:ACP transacylase | | Activates malonyl CoA for reaction with acetyl-ACP |
| (c) | 3-ketoacyl-ACP synthetase | | Reacts priming acetyl-ACP with chain-extending malonyl-ACP. |
| (d) | 3-ketoacyl-ACP reductase | | Reduces the carbon 3 ketone to a hydroxyl group |
| (e) | 3-Hydroxyacyl ACP dehydrase | | Removes water |
| (f) | Enoyl-ACP reductase | | Reduces the C2-C3 double bond. |

Abbreviations: RBS, ribosomal binding site; rcTE, acyl-ACP thioesterase from *R. communis*; MtG1, a $NAD^+$-dependent 3-oxoacyl-ACP reductase from *M. tuberculosis*; *lacI*, regulator gene of *trc* promoter system; *AmpR*, ampicillin resistant gene; T1 terminator and T2 terminator, transcriptional terminator of *rrnB*; pBR322 origin, origin of replication.

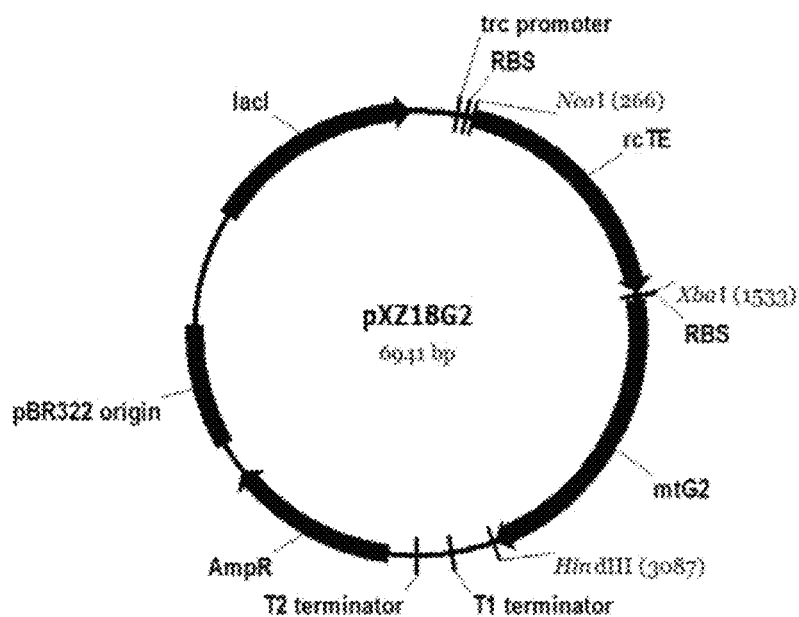

FIGURE 3A

Abbreviations: RBS, ribosomal binding site; rcTE, acyl-ACP thioesterase from *R. communis*; MtG2, a $NAD^+$-dependent 3-oxoacyl-ACP reductase from *M. tuberculosis* with an omission of the first 16 amino acids; *lacI*, regulator gene of *trc* promoter system; *AmpR*, ampicillin resistant gene; T1 terminator and T2 terminator, transcriptional terminator of *rrnB*; pBR322 origin, origin of replication.

FIGURE 4

SEQ ID NO: 1 (*Ricinus communis* palmitoyl-acyl carrier protein thioesterase (rcTE) from XM_002515518/XP_002515564

```
MVATAAAATSSFFPVPSQSADANFDKAPASLGGIKLKSTSCSRG
LQVKANAQAPPKINGSSVGFTTSVETVKNDGDMPLPPPPRTFINQLPDWSMLLAAITT
IFLAAEKQWMMLDWKPRRPDMLIDPFGIGRIVQDGLIFRQNFSIRSYEIGADRTASIE
TLMNHLQETALNHVKTAGLLGDGFGSTPEMSKRNLIWVVTRMQVLVDRYPTWGDVVQV
DTWVSKSGKNGMRRDWCVRDSRTGETLTRASSVWVMMNKLTRRLSKIPEEVRGEIEPY
FLNSDPIVDEDSRKLPKLDDSNADYVRKGLTPRWSDLDINQHVNNVKYIGWILESAPL
PILESHELSAITLEYRRECGRDSVLQSLTAVSGNGIGNLGNAGDIECQHLLRLEDGAE
IVRGRTEWRPKYSSNFGIMGQIPVESA
```

FIGURE 5

SEQ ID NO: 2 3-oxoacyl-ACP reductase FabG [EC:1.1.1.100] from Mycobacterium tuberculosis

```
MAPKRSSDLFSQVVNSGPGSFLARQLGVPQPETLRRYRAGEPPLTGSLLIGGAGRVVEPL
RAALEKDYDLVGNNLGGRWADSFGGLVFDATGITEPAGLKGLHEFFTPVLRNLGRCGRVV
VVGGTPEAAASTNERIAQRALEGFTRSLGKELRRGATTALVYLSPDAKPAATGLESTMRF
LLSAKSAYVDGQVFSVGADDSTPPADWEKPLDGKVAIVTGAARGIGATIAEVFARDGAHV
VAIDVESAAENLAETASKVGGTALWLDVTADDAVDKISEHLRDHHGGKADILVNNAGITR
DKLLANMDDARWDAVLAVNLLAPLRLTEGLVGNGSIGEGGRVIGLSSIAGIAGNRGQTNY
ATTKAGMIGITQALAPGLAAKGITINAVAPGFIETQMTAAIPLATREVGRRLNSLLQGGQ
PVDVAEAIAYFASPASNAVTGNVIRVCGQAMIGA
```

FIGURE 6

SEQ ID NO: 3 3-oxoacyl-ACP reductase FabG [EC:1.1.1.100] from Mycobacterium tuberculosis

```
GPGSFLARQLGVPQPETLRRYRAGEPPLTGSLLIGGAGRVVEPLRAALEKDYDLVGNNLG
GRWADSFGGLVFDATGITEPAGLKGLHEFFTPVLRNLGRCGRVVVVGGTPEAAASTNERI
AQRALEGFTRSLGKELRRGATTALVYLSPDAKPAATGLESTMRFLLSAKSAYVDGQVFSV
GADDSTPPADWEKPLDGKVAIVTGAARGIGATIAEVFARDGAHVVAIDVESAAENLAETA
SKVGGTALWLDVTADDAVDKISEHLRDHHGGKADILVNNAGITRDKLLANMDDARWDAVL
AVNLLAPLRLTEGLVGNGSIGEGGRVIGLSSIAGIAGNRGQTNYATTKAGMIGITQALAP
GLAAKGITINAVAPGFIETQMTAAIPLATREVGRRLNSLLQGGQPVDVAEAIAYFASPAS
NAVTGNVIRVCGQAMIGA
```

FIGURE 7

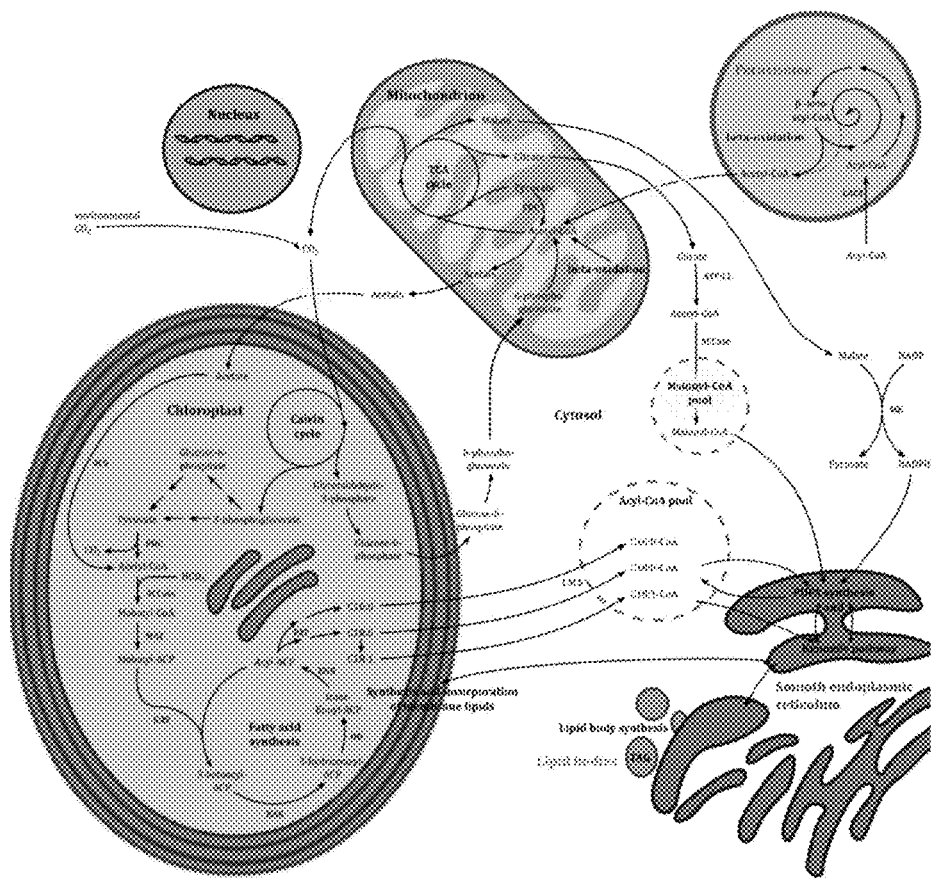

Simplified overview of the compartments, the main pathways and the metabolites in most Chromista; calvin cycle, fatty acid synthesis, tricarboxylic acid cycle, polyunsaturated FA pathway, β-oxidation and lipid synthesis shown in black arrows. Involved enzymes are shown in red: ACCase, acetyl-CoA carboxylase; ACS, Acyl-CoA synthetase, ACP, acyl carrier protein; CoA, coenzyme A; ATP:CL, ATP-citrate lyase; ENR, enoyl-ACP reductase; FAT, fatty acyl-ACP thioesterase; HD, 3-hydroxyacyl-ACP dehydratase; KAR, 3-ketoacyl-ACP reductase; KAS, 3-ketoacyl-ACP synthase; LACS, long chain acyl CoA synthetase; MAT, malonyl-CoA:ACP transacylase; ME, malic enzyme; PDC, pyruvate dehydrogenase complex; PUFA, polyunsaturated fatty acid; TAG, triacylglyceride; TCA, tricarboxylic acid. Different MEs possess different localizations (plastidial, mitochondrial). For simplicity, ME is placed in the cytosol.

AAA: restriction site
AAA: terminator
AAA: promoter
aaa: FabG antisense sequence

AS3

<u>GGTACC</u>GGCTGTTTTGGCGGATGAGAGAAGATTTTCAGCCTGATACAGATTA
AATCAGAACGCAGAAGCGGTCTGATAAAACAGAATTTGCCTGGCGGCAGTA
GCGCGGTGGTCCCACCTGACCCCATGCCGAACTCAGAAGTGAAACGCCGTA
GCGCCGATGGTAGTGTGGGGTCTCCCCATGCGAGAGTAGGGAACTGCCAGG
CATCAAATAAAACGAAAGGCTCAGTCGAAAGACTGGGCCTTTCGTTTTATCT
GTTGTTTGTCGGTGAACGCTCTCCTGAGTAGGACAAATCCGCCGGGAGCGG
ATTTGAACGTTGCGAAGCAACGGCCCGGAGGGTGGCGGGCAGGACGCCCG
CCATAAACTGCCAGGCATCAAATTAAGCAGAAGGCCATCCTGACGGATGGC
CTTTTTGCGTTTCTAC**GCTTATCATCGACTGCACGGTGCACCAATGCTTCTGGCG
TCAGGCAGCCATCGGAAGCTGTGGTATGGCTGTGCAGGTCGTAAATCACTGCAT
AATTCGTGTCGCTCAAGGCGCACTCCCGTTCTGGATAATGTTTTTTGCGCCGACA
TCATAACGGTTCTGGCAAATATTCTGAAATGAGCTGTTGACAATTAATCATCCGG
CTCGTATAATGTGTGGAATTGTGAGCGGATAACAATTTCACACAGGAAACAGAC**
Cttatttcgggcctcgttgttgcaaatgtcattatggcgcactgcgttgaagcgcgcggtca
ctaaatgacttcggctagttcgggcgaaagcggcgtcgcatcaaccggactggcggtaaagg
gtaccatggttggtgtcttggctatcactattatgctggtactgcgaaaaagtagtatcgcg
cgtaatggcgaaaactgtctgccttttgtctactttccaaccaaagctattatagcaaggtg
agaagtagaaagtaagcgtaattgtccaatagtgctcactatggccgtaataactggtccta
taggtgaagtggtttaagacgcgcttaaaaaggtcttgtctaagctatctacggcccagcc
agtgtaagttgtagtctggaaacggcaac<u>AAGCTT</u>

FIGURE 12A

AAA: restriction site
AAA: terminator
AAA: promoter
aaa: FabG antisense sequence

AS2

GGTACCGGCTGTTTTGGCGGATGAGAGAAGATTTTCAGCCTGATACAGATTA
AATCAGAACGCAGAAGCGGTCTGATAAAACAGAATTTGCCTGGCGGCAGTA
GCGCGGTGGTCCCACCTGACCCCATGCCGAACTCAGAAGTGAAACGCCGTA
GCGCCGATGGTAGTGTGGGGTCTCCCCATGCGAGAGTAGGGAACTGCCAGG
CATCAAATAAAACGAAAGGCTCAGTCGAAAGACTGGGCCTTTCGTTTTATCT
GTTGTTTGTCGGTGAACGCTCTCCTGAGTAGGACAAATCCGCCGGGAGCGG
ATTTGAACGTTGCGAAGCAACGGCCCGGAGGGTGGCGGGCAGGACGCCCG
CCATAAACTGCCAGGCATCAAATTAAGCAGAAGGCCATCCTGACGGATGGC
CTTTTTGCGTTTCTACGCTTATCATCGACTGCACGGTGCACCAATGCTTCTGGCG
TCAGGCAGCCATCGGAAGCTGTGGTATGGCTGTGCAGGTCGTAAATCACTGCAT
AATTCGTGTCGCTCAAGGCGCACTCCCGTTCTGGATAATGTTTTTTGCGCCGACA
TCATAACGGTTCTGGCAAATATTCTGAAATGAGCTGTTGACAATTAATCATCCGG
CTCGTATAATGTGTGGAATTGTGAGCGGATAACAATTTCACACAGGAAACAGAC
Cttattatgctggtactgcgaaaaagtagtatcgcgcgtaatggcgaaaactgtctgcctttt
tgtctactttccaaccaaagctattatagcaaggtgagaagtagaaagtaagcgtaattgtc
caatagtgctcactatggccgtaataactggtcctataggtgaagtggtttaagacgcgctt
aaaaaggtcttgtctaagctatctacggcccagccagtgtaagttgtagtctggaaacggc
aacAAGCTT

FIGURE 12B

AAA: restriction site
AAA: terminator
AAA: promoter
aaa: FabG antisense sequence

AS3

GGTACCGGCTGTTTTGGCGGATGAGAGAAGATTTTCAGCCTGATACAGATTA
AATCAGAACGCAGAAGCGGTCTGATAAAACAGAATTTGCCTGGCGGCAGTA
GCGCGGTGGTCCCACCTGACCCCATGCCGAACTCAGAAGTGAAACGCCGTA
GCGCCGATGGTAGTGTGGGGTCTCCCCATGCGAGAGTAGGGAACTGCCAGG
CATCAAATAAAACGAAAGGCTCAGTCGAAAGACTGGGCCTTTCGTTTTATCT
GTTGTTTGTCGGTGAACGCTCTCCTGAGTAGGACAAATCCGCCGGGAGCGG
ATTTGAACGTTGCGAAGCAACGGCCCGGAGGGTGGCGGGCAGGACGCCCG
CCATAAACTGCCAGGCATCAAATTAAGCAGAAGGCCATCCTGACGGATGGC
CTTTTTGCGTTTCTACGCTTATCATCGACTGCACGGTGCACCAATGCTTCTGGCG
TCAGGCAGCCATCGGAAGCTGTGGTATGGCTGTGCAGGTCGTAAATCACTGCAT
AATTCGTGTCGCTCAAGGCGCACTCCCGTTCTGGATAATGTTTTTTGCGCCGACA
TCATAACGGTTCTGGCAAATATTCTGAAATGAGCTGTTGACAATTAATCATCCGG
CTCGTATAATGTGTGGAATTGTGAGCGGATAACAATTTCACACAGGAAACAGAC
Ctgtagaaagtaagcgtaattgtccaatagtgctcactatggccgtaataactggtcctata
ggtgaagtggtttaagacgcgcttaaaaaggtcttgtctaagctatctacggcccagccag
tgtaagttgtagtctggaaacggcaacAAGCTT

FIGURE 12C

AAA: restriction site
AAA: terminator
AAA: promoter
AAA: paired termini
aaa: FabG antisense sequence AS1-Looped GGTACCGGCTGTTTTGGCGGATGAGAGAAGATTTTCAGCCTGATACAGATTA
AATCAGAACGCAGAAGCGGTCTGATAAAACAGAATTTGCCTGGCGGCAGTA
GCGCGGTGGTCCCACCTGACCCCATGCCGAACTCAGAAGTGAAACGCCGTA
GCGCCGATGGTAGTGTGGGGTCTCCCCATGCGAGAGTAGGGAACTGCCAGG
CATCAAATAAAACGAAAGGCTCAGTCGAAAGACTGGGCCTTTCGTTTTATCT
GTTGTTTGTCGGTGAACGCTCTCCTGAGTAGGACAAATCCGCCGGGAGCGG
ATTTGAACGTTGCGAAGCAACGGCCCGGAGGGTGGCGGGCAGGACGCCCG
CCATAAACTGCCAGGCATCAAATTAAGCAGAAGGCCATCCTGACGGATGGC
CTTTTGCGTTTCTACGCTTATCATCGACTGCACGGTGCACCAATGCTTCTGGCG
TCAGGCAGCCATCGGAAGCTGTGGTATGGCTGTGCAGGTCGTAAATCACTGCAT
AATTCGTGTCGCTCAAGGCGCACTCCCGTTCTGGATAATGTTTTTTGCGCCGACA
TCATAACGGTTCTGGCAAATATTCTGAAATGAGCTGTTGACAATTAATCATCCGG
CTCGTATAATGTGTGGAATTGTGAGCGGATAACAATTTCACACAGGAAACAGAC
CAGGAGGAATTAACCATGCAGTGGTGGTGGTGGTGGTGGAGCTCttatttcgg
gcctcgttgttgcaaatgtcattatggcgcactgcgttgaagcgcgcggtcactaaatgact
tcggctagttcgggcgaaagcggcgtcgcatcaaccggactggcggtaaagggtaccatggt
tggtgtcttggctatcactattatgctggtactgcgaaaaagtagtatcgcgcgtaatggcg
aaaactgtctgccttttgtctactttccaaccaaagctattatagcaaggtgagaagtagaa
agtaagcgtaattgtccaatagtgctcactatggccgtaataactggtcctataggtgaagt
ggtttaagacgcgcttaaaaaaggtcttgtctaagctatctacggcccagccagtgtaagtt
gtagtctggaaacggcaacCTCGAGCACCACCACCACCACCACTGCATGGTTAAT
TCCTCCTGGATCC

FIGURE 13A

AAA: restriction site
AAA: terminator
AAA: promoter
AAA: paired termini
aaa: FabG antisense sequence AS2-Looped GGTACCGGCTGTTTTGGCGGATGAGAGAAGATTTTCAGCCTGATACAGATTA
AATCAGAACGCAGAAGCGGTCTGATAAAACAGAATTTGCCTGGCGGCAGTA
GCGCGGTGGTCCCACCTGACCCCATGCCGAACTCAGAAGTGAAACGCCGTA
GCGCCGATGGTAGTGTGGGGTCTCCCCATGCGAGAGTAGGGAACTGCCAGG
CATCAAATAAAACGAAAGGCTCAGTCGAAAGACTGGGCCTTTCGTTTTATCT
GTTGTTTGTCGGTGAACGCTCTCCTGAGTAGGACAAATCCGCCGGGAGCGG
ATTTGAACGTTGCGAAGCAACGGCCCGGAGGGTGGCGGGCAGGACGCCCG
CCATAAACTGCCAGGCATCAAATTAAGCAGAAGGCCATCCTGACGGATGGC
CTTTTTGCGTTTCTACGCTTATCATCGACTGCACGGTGCACCAATGCTTCTGGCG
TCAGGCAGCCATCGGAAGCTGTGGTATGGCTGTGCAGGTCGTAAATCACTGCAT
AATTCGTGTCGCTCAAGGCGCACTCCCGTTCTGGATAATGTTTTTTGCGCCGACA
TCATAACGGTTCTGGCAAATATTCTGAAATGAGCTGTTGACAATTAATCATCCGG
CTCGTATAATGTGTGGAATTGTGAGCGGATAACAATTTCACACAGGAAACAGAC
CAGGAGGAATTAACCATGCAGTGGTGGTGGTGGTGGAGCTCttattatgc
tggtactgcgaaaaagtagtatcgcgcgtaatggcgaaaactgtctgccttttgtctactt
ccaaccaaagctattatagcaaggtgagaagtagaaagtaagcgtaattgtccaatagtgct
cactatggccgtaataactggtcctataggtgaagtggtttaagacgcgcttaaaaaaggtc
ttgtctaagctatctacggcccagccagtgtaagttgtagtctggaaacggcaacCTCGAG
CACCACCACCACCACCACTGCATGGTTAATTCCTCCTGGATCC

FIGURE 13B

AS3-Looped

AAA: restriction site
AAA: terminator
AAA: promoter
AAA: paired termini
aaa: FabG antisense sequence GGTACCGGCTGTTTTGGCGGATGAGAGAAGATTTTCAGCCTGATACAGATTA
AATCAGAACGCAGAAGCGGTCTGATAAAACAGAATTTGCCTGGCGGCAGTA
GCGCGGTGGTCCCACCTGACCCCATGCCGAACTCAGAAGTGAAACGCCGTA
GCGCCGATGGTAGTGTGGGGTCTCCCCATGCGAGAGTAGGGAACTGCCAGG
CATCAAATAAAACGAAAGGCTCAGTCGAAAGACTGGGCCTTTCGTTTTATCT
GTTGTTTGTCGGTGAACGCTCTCCTGAGTAGGACAAATCCGCCGGGAGCGG
ATTTGAACGTTGCGAAGCAACGGCCCGGAGGGTGGCGGGCAGGACGCCCG
CCATAAACTGCCAGGCATCAAATTAAGCAGAAGGCCATCCTGACGGATGGC
CTTTTTGCGTTTCTACGCTTATCATCGACTGCACGGTGCACCAATGCTTCTGGCG
TCAGGCAGCCATCGGAAGCTGTGGTATGGCTGTGCAGGTCGTAAATCACTGCAT
AATTCGTGTCGCTCAAGGCGCACTCCCGTTCTGGATAATGTTTTTTGCGCCGACA
TCATAACGGTTCTGGCAAATATTCTGAAATGAGCTGTTGACAATTAATCATCCGG
CTCGTATAATGTGTGGAATTGTGAGCGGATAACAATTTCACACAGGAAACAGAC
CAGGAGGAATTAACCATGCAGTGGTGGTGGTGGTGGTGGAGCTCtgtagaaag
taagcgtaattgtccaatagtgctcactatggccgtaataactggtcctataggtgaagtgg
tttaagacgcgcttaaaaaggtcttgtctaagctatctacggcccagccagtgtaagttgt
agtctggaaacggcaacCTCGAGCACCACCACCACCACCACTGCATGGTTAATTC
CTCCTGGATCC

FIGURE 13C

SEQUENCE LISTING

<160> NUMBER OF SEQ ID NOS: 9

<210> SEQ ID NO 1
<211> LENGTH: 419
<212> TYPE: PRT
<213> ORGANISM: Ricinus communis

<400> SEQUENCE: 1

```
Met Val Ala Thr Ala Ala Ala Thr Ser Ser Phe Phe Pro Val Pro
1               5                   10                  15

Ser Gln Ser Ala Asp Ala Asn Phe Asp Lys Ala Pro Ala Ser Leu Gly
                20                  25                  30

Gly Ile Lys Leu Lys Ser Thr Ser Cys Ser Arg Gly Leu Gln Val Lys
                35                  40                  45

Ala Asn Ala Gln Ala Pro Pro Lys Ile Asn Gly Ser Ser Val Gly Phe
        50                  55                  60

Thr Thr Ser Val Glu Thr Val Lys Asn Asp Gly Asp Met Pro Leu Pro
65                  70                  75                  80

Pro Pro Pro Arg Thr Phe Ile Asn Gln Leu Pro Asp Trp Ser Met Leu
                85                  90                  95

Leu Ala Ala Ile Thr Thr Ile Phe Leu Ala Ala Glu Lys Gln Trp Met
                100                 105                 110

Met Leu Asp Trp Lys Pro Arg Arg Pro Asp Met Leu Ile Asp Pro Phe
                115                 120                 125

Gly Ile Gly Arg Ile Val Gln Asp Gly Leu Ile Phe Arg Gln Asn Phe
        130                 135                 140

Ser Ile Arg Ser Tyr Glu Ile Gly Ala Asp Arg Thr Ala Ser Ile Glu
145                 150                 155                 160

Thr Leu Met Asn His Leu Gln Glu Thr Ala Leu Asn His Val Lys Thr
                165                 170                 175

Ala Gly Leu Leu Gly Asp Gly Phe Gly Ser Thr Pro Glu Met Ser Lys
                180                 185                 190

Arg Asn Leu Ile Trp Val Val Thr Arg Met Gln Val Leu Val Asp Arg
        195                 200                 205

Tyr Pro Thr Trp Gly Asp Val Val Gln Val Asp Thr Trp Val Ser Lys
        210                 215                 220

Ser Gly Lys Asn Gly Met Arg Arg Asp Trp Cys Val Arg Asp Ser Arg
225                 230                 235                 240

Thr Gly Glu Thr Leu Thr Arg Ala Ser Ser Val Trp Val Met Met Asn
                245                 250                 255

Lys Leu Thr Arg Arg Leu Ser Lys Ile Pro Glu Glu Val Arg Gly Glu
                260                 265                 270

Ile Glu Pro Tyr Phe Leu Asn Ser Asp Pro Ile Val Asp Glu Asp Ser
```

```
                275                 280                 285
Arg Lys Leu Pro Lys Leu Asp Asp Ser Asn Ala Asp Tyr Val Arg Lys
            290                 295                 300

Gly Leu Thr Pro Arg Trp Ser Asp Leu Asp Ile Asn Gln His Val Asn
305                 310                 315                 320

Asn Val Lys Tyr Ile Gly Trp Ile Leu Glu Ser Ala Pro Leu Pro Ile
                325                 330                 335

Leu Glu Ser His Glu Leu Ser Ala Ile Thr Leu Glu Tyr Arg Arg Glu
            340                 345                 350

Cys Gly Arg Asp Ser Val Leu Gln Ser Leu Thr Ala Val Ser Gly Asn
            355                 360                 365

Gly Ile Gly Asn Leu Gly Asn Ala Gly Asp Ile Glu Cys Gln His Leu
            370                 375                 380

Leu Arg Leu Glu Asp Gly Ala Glu Ile Val Arg Gly Arg Thr Glu Trp
385                 390                 395                 400

Arg Pro Lys Tyr Ser Ser Asn Phe Gly Ile Met Gly Gln Ile Pro Val
                405                 410                 415

Glu Ser Ala

<210> SEQ ID NO 2
<211> LENGTH: 454
<212> TYPE: PRT
<213> ORGANISM: Mycobacterium tuberculosis

<400> SEQUENCE: 2

Met Ala Pro Lys Arg Ser Ser Asp Leu Phe Ser Gln Val Val Asn Ser
1               5                   10                  15

Gly Pro Gly Ser Phe Leu Ala Arg Gln Leu Gly Val Pro Gln Pro Glu
            20                  25                  30

Thr Leu Arg Arg Tyr Arg Ala Gly Glu Pro Pro Leu Thr Gly Ser Leu
        35                  40                  45

Leu Ile Gly Gly Ala Gly Arg Val Val Glu Pro Leu Arg Ala Ala Leu
    50                  55                  60

Glu Lys Asp Tyr Asp Leu Val Gly Asn Asn Leu Gly Gly Arg Trp Ala
65                  70                  75                  80

Asp Ser Phe Gly Gly Leu Val Phe Asp Ala Thr Gly Ile Thr Glu Pro
                85                  90                  95

Ala Gly Leu Lys Gly Leu His Glu Phe Phe Thr Pro Val Leu Arg Asn
            100                 105                 110

Leu Gly Arg Cys Gly Arg Val Val Val Gly Gly Thr Pro Glu Ala
            115                 120                 125

Ala Ala Ser Thr Asn Glu Arg Ile Ala Gln Arg Ala Leu Glu Gly Phe
            130                 135                 140

Thr Arg Ser Leu Gly Lys Glu Leu Arg Arg Gly Ala Thr Thr Ala Leu
145                 150                 155                 160

Val Tyr Leu Ser Pro Asp Ala Lys Pro Ala Thr Gly Leu Glu Ser
                165                 170                 175

Thr Met Arg Phe Leu Leu Ser Ala Lys Ser Ala Tyr Val Asp Gly Gln
            180                 185                 190

Val Phe Ser Val Gly Ala Asp Ser Thr Pro Ala Asp Trp Glu
            195                 200                 205

Lys Pro Leu Asp Gly Lys Val Ala Ile Val Thr Gly Ala Ala Arg Gly
            210                 215                 220

Ile Gly Ala Thr Ile Ala Glu Val Phe Ala Arg Asp Gly Ala His Val
```

```
                    225                 230                 235                 240

Val Ala Ile Asp Val Glu Ser Ala Ala Glu Asn Leu Ala Glu Thr Ala
                        245                 250                 255

Ser Lys Val Gly Gly Thr Ala Leu Trp Leu Asp Val Thr Ala Asp Asp
                        260                 265                 270

Ala Val Asp Lys Ile Ser Glu His Leu Arg Asp His His Gly Gly Lys
                        275                 280                 285

Ala Asp Ile Leu Val Asn Asn Ala Gly Ile Thr Arg Asp Lys Leu Leu
                        290                 295                 300

Ala Asn Met Asp Asp Ala Arg Trp Asp Ala Val Leu Ala Val Asn Leu
        305                 310                 315                 320

Leu Ala Pro Leu Arg Leu Thr Glu Gly Leu Val Gly Asn Gly Ser Ile
                        325                 330                 335

Gly Glu Gly Gly Arg Val Ile Gly Leu Ser Ser Ile Ala Gly Ile Ala
                        340                 345                 350

Gly Asn Arg Gly Gln Thr Asn Tyr Ala Thr Thr Lys Ala Gly Met Ile
                        355                 360                 365

Gly Ile Thr Gln Ala Leu Ala Pro Gly Leu Ala Ala Lys Gly Ile Thr
                        370                 375                 380

Ile Asn Ala Val Ala Pro Gly Phe Ile Glu Thr Gln Met Thr Ala Ala
        385                 390                 395                 400

Ile Pro Leu Ala Thr Arg Glu Val Gly Arg Arg Leu Asn Ser Leu Leu
                        405                 410                 415

Gln Gly Gly Gln Pro Val Asp Val Ala Glu Ile Ala Tyr Phe Ala
                        420                 425                 430

Ser Pro Ala Ser Asn Ala Val Thr Gly Asn Val Ile Arg Val Cys Gly
                        435                 440                 445

Gln Ala Met Ile Gly Ala
                        450

<210> SEQ ID NO 3
<211> LENGTH: 438
<212> TYPE: PRT
<213> ORGANISM: Mycobacterium tuberculosis

<400> SEQUENCE: 3

Gly Pro Gly Ser Phe Leu Ala Arg Gln Leu Gly Val Pro Gln Pro Glu
        1               5                   10                  15

Thr Leu Arg Arg Tyr Arg Ala Gly Glu Pro Pro Leu Thr Gly Ser Leu
                        20                  25                  30

Leu Ile Gly Gly Ala Gly Arg Val Glu Pro Leu Arg Ala Ala Leu
                        35                  40                  45

Glu Lys Asp Tyr Asp Leu Val Gly Asn Asn Leu Gly Gly Arg Trp Ala
        50                  55                  60

Asp Ser Phe Gly Gly Leu Val Phe Asp Ala Thr Gly Ile Thr Glu Pro
        65                  70                  75                  80

Ala Gly Leu Lys Gly Leu His Glu Phe Phe Thr Pro Val Leu Arg Asn
                        85                  90                  95

Leu Gly Arg Cys Gly Arg Val Val Val Val Gly Gly Thr Pro Glu Ala
                        100                 105                 110

Ala Ala Ser Thr Asn Glu Arg Ile Ala Gln Arg Ala Leu Glu Gly Phe
                        115                 120                 125

Thr Arg Ser Leu Gly Lys Glu Leu Arg Arg Gly Ala Thr Thr Ala Leu
                        130                 135                 140
```

Val Tyr Leu Ser Pro Asp Ala Lys Pro Ala Thr Gly Leu Glu Ser
145                 150                 155                 160

Thr Met Arg Phe Leu Leu Ser Ala Lys Ser Ala Tyr Val Asp Gly Gln
                165                 170                 175

Val Phe Ser Val Gly Ala Asp Asp Ser Thr Pro Pro Ala Asp Trp Glu
            180                 185                 190

Lys Pro Leu Asp Gly Lys Val Ala Ile Val Thr Gly Ala Ala Arg Gly
        195                 200                 205

Ile Gly Ala Thr Ile Ala Glu Val Phe Ala Arg Asp Gly Ala His Val
210                 215                 220

Val Ala Ile Asp Val Glu Ser Ala Ala Glu Asn Leu Ala Glu Thr Ala
225                 230                 235                 240

Ser Lys Val Gly Gly Thr Ala Leu Trp Leu Asp Val Thr Ala Asp Asp
                245                 250                 255

Ala Val Asp Lys Ile Ser Glu His Leu Arg Asp His His Gly Gly Lys
            260                 265                 270

Ala Asp Ile Leu Val Asn Asn Ala Gly Ile Thr Arg Asp Lys Leu Leu
        275                 280                 285

Ala Asn Met Asp Asp Ala Arg Trp Asp Ala Val Leu Ala Val Asn Leu
290                 295                 300

Leu Ala Pro Leu Arg Leu Thr Glu Gly Leu Val Gly Asn Gly Ser Ile
305                 310                 315                 320

Gly Glu Gly Gly Arg Val Ile Gly Leu Ser Ser Ile Ala Gly Ile Ala
                325                 330                 335

Gly Asn Arg Gly Gln Thr Asn Tyr Ala Thr Thr Lys Ala Gly Met Ile
            340                 345                 350

Gly Ile Thr Gln Ala Leu Ala Pro Gly Leu Ala Ala Lys Gly Ile Thr
        355                 360                 365

Ile Asn Ala Val Ala Pro Gly Phe Ile Glu Thr Gln Met Thr Ala Ala
370                 375                 380

Ile Pro Leu Ala Thr Arg Glu Val Gly Arg Arg Leu Asn Ser Leu Leu
385                 390                 395                 400

Gln Gly Gly Gln Pro Val Asp Val Ala Glu Ala Ile Ala Tyr Phe Ala
                405                 410                 415

Ser Pro Ala Ser Asn Ala Val Thr Gly Asn Val Ile Arg Val Cys Gly
            420                 425                 430

Gln Ala Met Ile Gly Ala
        435

<210> SEQ ID NO 4
<211> LENGTH: 1089
<212> TYPE: DNA
<213> ORGANISM: Artificial Sequence
<220> FEATURE:
<223> OTHER INFORMATION: Artificial sequence for generating an
      anti-sense RNA.

<400> SEQUENCE: 4
ggtaccggct gttttggcgg atgagagaag attttcagcc tgatacagat taaatcagaa      60
cgcagaagcg gtctgataaa acagaatttg cctggcggca gtagcgcggt ggtcccacct     120
gaccccatgc cgaactcaga agtgaaacgc cgtagcgccg atggtagtgt ggggtctccc     180
catgcgagag tagggaactg ccaggcatca aataaaacga aaggctcagt cgaaagactg     240
ggcctttcgt tttatctgtt gtttgtcggt gaacgctctc ctgagtagga caaatccgcc     300
gggagcggat ttgaacgttg cgaagcaacg gcccggaggg tggcgggcag gacgcccgcc     360

```
ataaactgcc aggcatcaaa ttaagcagaa ggccatcctg acggatggcc tttttgcgtt      420
tctacgctta tcatcgactg cacggtgcac caatgcttct ggcgtcaggc agccatcgga      480
agctgtggta tggctgtgca ggtcgtaaat cactgcataa ttcgtgtcgc tcaaggcgca      540
ctcccgttct ggataatgtt ttttgcgccg acatcataac ggttctggca aatattctga      600
aatgagctgt tgacaattaa tcatccggct cgtataatgt gtggaattgt gagcggataa      660
caatttcaca caggaaacag acctattttc gggcctcgtt gttgcaaatg tcattatggc      720
gcactgcgtt gaagcgcgcg gtcactaaat gacttcggct agttcgggcg aaagcggcgt      780
cgcatcaacc ggactggcgg taaagggtac catggttggt gtcttggcta tcactattat      840
gctggtactg cgaaaaagta gtatcgcgcg taatggcgaa aactgtctgc cttttgtcta      900 cttttccaacc aaagctatta tagcaaggtg agaagtagaa agtaagcgta attgtccaat      960
agtgctcact atggccgtaa taactggtcc tataggtgaa gtggtttaag acgcgcttaa     1020
aaaaggtctt gtctaagcta tctacggccc agccagtgta agttgtagtc tggaaacggc     1080
aacaagctt                                                             1089

<210> SEQ ID NO 5
<211> LENGTH: 939
<212> TYPE: DNA
<213> ORGANISM: Artificial Sequence
<220> FEATURE:
<223> OTHER INFORMATION: Artificial sequence for generating anti-sense
      RNA

<400> SEQUENCE: 5
ggtaccggct gttttggcgg atgagagaag attttcagcc tgatacagat taaatcagaa       60
cgcagaagcg gtctgataaa acagaatttg cctggcggca gtagcgcggt ggtcccacct      120
gaccccatgc cgaactcaga agtgaaacgc cgtagcgccg atggtagtgt ggggtctccc      180
catgcgagag tagggaactg ccaggcatca aataaaacga aaggctcagt cgaaagactg      240
ggcctttcgt tttatctgtt gtttgtcggt gaacgctctc ctgagtagga caaatccgcc      300
gggagcggat ttgaacgttg cgaagcaacg gcccggaggg tggcgggcag gacgcccgcc      360
ataaactgcc aggcatcaaa ttaagcagaa ggccatcctg acggatggcc tttttgcgtt      420
tctacgctta tcatcgactg cacggtgcac caatgcttct ggcgtcaggc agccatcgga      480
agctgtggta tggctgtgca ggtcgtaaat cactgcataa ttcgtgtcgc tcaaggcgca      540
ctcccgttct ggataatgtt ttttgcgccg acatcataac ggttctggca aatattctga      600
aatgagctgt tgacaattaa tcatccggct cgtataatgt gtggaattgt gagcggataa      660
caatttcaca caggaaacag acctattat gctggtactg cgaaaaagta gtatcgcgcg       720
taatggcgaa aactgtctgc cttttgtcta ctttccaacc aaagctatta tagcaaggtg      780
agaagtagaa agtaagcgta attgtccaat agtgctcact atggccgtaa taactggtcc      840
tataggtgaa gtggtttaag acgcgcttaa aaaaggtctt gtctaagcta tctacggccc      900
agccagtgta agttgtagtc tggaaacggc aacaagctt                             939

<210> SEQ ID NO 6
<211> LENGTH: 839
<212> TYPE: DNA
<213> ORGANISM: Artificial Sequence
<220> FEATURE:
<223> OTHER INFORMATION: Artificial sequence for generating anti-sense
      RNA
```

```
<400> SEQUENCE: 6
ggtaccggct gttttggcgg atgagagaag attttcagcc tgatacagat taaatcagaa      60
cgcagaagcg gtctgataaa acagaatttg cctggcggca gtagcgcggt ggtcccacct     120
gaccccatgc cgaactcaga agtgaaacgc cgtagcgccg atggtagtgt ggggtctccc     180
catgcgagag tagggaactg ccaggcatca aataaaacga aaggctcagt cgaaagactg     240
ggcctttcgt tttatctgtt gtttgtcggt gaacgctctc ctgagtagga caaatccgcc     300
gggagcggat ttgaacgttg cgaagcaacg gcccggaggg tggcgggcag gacgcccgcc     360
ataaactgcc aggcatcaaa ttaagcagaa ggccatcctg acggatggcc ttttttgcgtt    420 tctacgctta tcatcgactg cacggtgcac caatgcttct ggcgtcaggc agccatcgga     480
agctgtggta tggctgtgca ggtcgtaaat cactgcataa ttcgtgtcgc tcaaggcgca     540
ctcccgttct ggataatgtt ttttgcgccg acatcataac ggttctggca aatattctga     600
aatgagctgt tgacaattaa tcatccggct cgtataatgt gtggaattgt gagcggataa     660
caatttcaca caggaaacag acctgtagaa agtaagcgta attgtccaat agtgctcact     720
atggccgtaa taactggtcc tataggtgaa gtggtttaag acgcgcttaa aaaaggtctt     780
gtctaagcta tctacggccc agccagtgta agttgtagtc tggaaacggc aacaagctt     839

<210> SEQ ID NO 7
<211> LENGTH: 1175
<212> TYPE: DNA
<213> ORGANISM: Artificial Sequence
<220> FEATURE:
<223> OTHER INFORMATION: Artificial sequence for generating anti-sense
      RNA

<400> SEQUENCE: 7
ggtaccggct gttttggcgg atgagagaag attttcagcc tgatacagat taaatcagaa      60
cgcagaagcg gtctgataaa acagaatttg cctggcggca gtagcgcggt ggtcccacct     120
gaccccatgc cgaactcaga agtgaaacgc cgtagcgccg atggtagtgt ggggtctccc     180
catgcgagag tagggaactg ccaggcatca aataaaacga aaggctcagt cgaaagactg     240
ggcctttcgt tttatctgtt gtttgtcggt gaacgctctc ctgagtagga caaatccgcc     300
gggagcggat ttgaacgttg cgaagcaacg gcccggaggg tggcgggcag gacgcccgcc     360
ataaactgcc aggcatcaaa ttaagcagaa ggccatcctg acggatggcc ttttttgcgtt    420 tctacgctta tcatcgactg cacggtgcac caatgcttct ggcgtcaggc agccatcgga     480
agctgtggta tggctgtgca ggtcgtaaat cactgcataa ttcgtgtcgc tcaaggcgca     540
ctcccgttct ggataatgtt ttttgcgccg acatcataac ggttctggca aatattctga     600
aatgagctgt tgacaattaa tcatccggct cgtataatgt gtggaattgt gagcggataa     660
caatttcaca caggaaacag accaggagga attaaccatg cagtggtggt ggtggtggtg     720
gagctcttat ttcgggcctc gttgttgcaa atgtcattat ggcgcactgc gttgaagcgc     780
gcggtcacta aatgacttcg gctagttcgg gcgaaagcgg cgtcgcatca accggactgg     840
cggtaaaggg taccatggtt ggtgtcttgg ctatcactat tatgctggta ctgcgaaaaa     900
gtagtatcgc gcgtaatggc gaaaactgtc tgccttttgt ctactttcca accaaagcta     960
ttatagcaag gtgagaagta gaaagtaagc gtaattgtcc aatagtgctc actatggccg    1020
taataactgg tcctataggt gaagtggttt aagacgcgct taaaaaaggt cttgtctaag    1080
ctatctacgg cccagccagt gtaagttgta gtctggaaac ggcaacctcg agcaccacca    1140
```

```
ccaccaccac tgcatggtta attcctcctg gatcc                                1175
```

<210> SEQ ID NO 8
<211> LENGTH: 1025
<212> TYPE: DNA
<213> ORGANISM: Artificial Sequence
<220> FEATURE:
<223> OTHER INFORMATION: Artificial sequence for generating anti-sense
      RNA

<400> SEQUENCE: 8

```
ggtaccggct gttttggcgg atgagagaag attttcagcc tgatacagat taaatcagaa      60
cgcagaagcg gtctgataaa acagaatttg cctggcggca gtagcgcggt ggtcccacct     120
gaccccatgc cgaactcaga agtgaaacgc cgtagcgccg atggtagtgt ggggtctccc     180
catgcgagag tagggaactg ccaggcatca aataaaacga aaggctcagt cgaaagactg     240
ggcctttcgt tttatctgtt gtttgtcggt gaacgctctc ctgagtagga caaatccgcc     300
gggagcggat ttgaacgttg cgaagcaacg gcccggaggg tggcgggcag gacgcccgcc     360
ataaactgcc aggcatcaaa ttaagcagaa ggccatcctg acggatggcc ttttttgcgtt     420
tctacgctta tcatcgactg cacggtgcac caatgcttct ggcgtcaggc agccatcgga     480
agctgtggta tggctgtgca ggtcgtaaat cactgcataa ttcgtgtcgc tcaaggcgca     540
ctcccgttct ggataatgtt ttttgcgccg acatcataac ggttctggca aatattctga     600
aatgagctgt tgacaattaa tcatccggct cgtataatgt gtggaattgt gagcggataa     660
caatttcaca caggaaacag accaggagga ttaaccatg cagtggtggt ggtggtggtg     720
gagctcttat tatgctggta ctgcgaaaaa gtagtatcgc gcgtaatggc gaaaactgtc     780
tgccttttgt ctactttcca accaaagcta ttatagcaag gtgagaagta gaaagtaagc     840
gtaattgtcc aatagtgctc actatggccg taataactgg tcctataggt gaagtggttt     900
aagacgcgct taaaaaggt cttgtctaag ctatctacgg cccagccagt gtaagttgta     960
gtctggaaac ggcaaccctcg agcaccacca ccaccaccac tgcatggtta attcctcctg    1020
gatcc                                                                1025
```

<210> SEQ ID NO 9
<211> LENGTH: 925
<212> TYPE: DNA
<213> ORGANISM: Artificial Sequence
<220> FEATURE:
<223> OTHER INFORMATION: Artificial sequence for generating anti-sense
      RNA

<400> SEQUENCE: 9

```
ggtaccggct gttttggcgg atgagagaag attttcagcc tgatacagat taaatcagaa      60
cgcagaagcg gtctgataaa acagaatttg cctggcggca gtagcgcggt ggtcccacct     120
gaccccatgc cgaactcaga agtgaaacgc cgtagcgccg atggtagtgt ggggtctccc     180
catgcgagag tagggaactg ccaggcatca aataaaacga aaggctcagt cgaaagactg     240
ggcctttcgt tttatctgtt gtttgtcggt gaacgctctc ctgagtagga caaatccgcc     300
gggagcggat ttgaacgttg cgaagcaacg gcccggaggg tggcgggcag gacgcccgcc     360
ataaactgcc aggcatcaaa ttaagcagaa ggccatcctg acggatggcc ttttttgcgtt     420
tctacgctta tcatcgactg cacggtgcac caatgcttct ggcgtcaggc agccatcgga     480
agctgtggta tggctgtgca ggtcgtaaat cactgcataa ttcgtgtcgc tcaaggcgca     540
ctcccgttct ggataatgtt ttttgcgccg acatcataac ggttctggca aatattctga     600
```

```
aatgagctgt tgacaattaa tcatccggct cgtataatgt gtggaattgt gagcggataa    660
caatttcaca caggaaacag accaggagga attaaccatg cagtggtggt ggtggtggtg    720
gagctctgta gaaagtaagc gtaattgtcc aatagtgctc actatggccg taataactgg    780
tcctataggt gaagtggttt aagacgcgct taaaaaaggt cttgtctaag ctatctacgg    840
cccagccagt gtaagttgta gtctggaaac ggcaacctcg agcaccacca ccaccaccac    900
tgcatggtta attcctcctg gatcc                                          925
```

FATTY ACID PRODUCTIVITY

PRIOR RELATED APPLICATIONS

This application claims priority to U.S. Ser. No. 61/889,166, entitled "IMPROVED FATTY ACID PRODUCTIVITY" filed Oct. 10, 2013, and is a continuation-in-part of PCT/US14/59139, entitled "IMPROVED FATTY ACID PRODUCTIVITY" filed Oct. 6, 2014, and each is incorporated by reference herein in its entirety for all purposes.

FEDERALLY SPONSORED RESEARCH STATEMENT

This invention was made with government support under Grant Nos: 0813570 and 1246376 awarded by the National Science Foundation. The government has certain rights in the invention.

FIELD OF THE DISCLOSURE

The disclosure generally relates to a method of producing fatty acids, and more particularly to a method of improving the productivity of bacteria that produce fatty acids.

BACKGROUND OF THE DISCLOSURE

Fatty acids are aliphatic acids fundamental to energy production and storage, cellular structure and as intermediates in the biosynthesis of hormones and other biologically important molecules. They are synthesized by a series of decarboxylative Claisen condensation reactions from acetyl-CoA and malonyl-CoA. Following each round of elongation, the beta keto group is reduced to the fully saturated carbon chain by the sequential action of a ketoreductase, a dehydratase, and an enol reductase. The growing fatty acid chain is carried between these active sites while attached covalently to the phosphoantetheine prosthetic group of an acyl carrier protein (ACP), and is released by the action of a thioesterase (TE) upon reaching a carbon chain length of 16. FIG. 1 shows a simplified diagram of fatty acid synthesis in $E.\ coli$.

There are two principal classes of fatty acid synthases. Type I systems utilize a single large, multifunctional polypeptide. A Type I fatty acid synthase system is also found in the CMN group of bacteria (*Corynebacteria, Mycobacteria,* and *Nocardia*). In these bacteria, the FAS I system produces palmititic acid, and cooperates with the FASII system to produce a greater diversity of lipid products.

Type II fatty acid synthases (FASII) are found in prokaryotes, plants, fungi, and parasites, as well as in mitochondria. FASII is characterized by the use of the discrete, monofunctional enzymes for fatty acid synthesis. In contrast to the complex Type I fatty acid synthase that catalyzes multiple enzymatic steps, FASII uses individual enzymes to carry out the same steps.

The enzyme 3-oxoacyl-ACP reductase (or beta-ketoacyl-ACP reductase) uses NADPH as the coenzyme to carry out the following reaction (from BRENDA Enzyme Database):

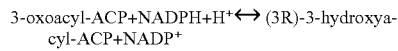

3-oxoacyl-ACP+NADPH+H$^+$ ⟷ (3R)-3-hydroxyacyl-ACP+NADP$^+$

However, the intracellular concentration of NADP$^+$ and NADPH is much lower than that of NAD$^+$ and NADH (Fuhrer and Sauer, 2009). Thus, at high fatty acid production rates, the NADPH availability can become a limiting factor, slowing production rates and overall accumulation.

Various strategies have been studied to increase NADPH availability in order to increase fatty acid productivity. These approaches have included: 1) the overexpression of a transhydrogenase enzyme that transfers the reducing power from NADH to NADPH (Sanchez et al., 2006), 2) the overexpression of NAD$^+$ kinase to increase the NADP concentration (Wang et al., 2013), or 3) the replacement of the native NAD$^+$ dependent glyceraldehyde-3-phosphate dehydrogenase (Gap) with a NADP$^+$ dependent Gap (Martinez et al., 2008).

However, there is always room for further improvement in this area, particularly as petroleum resources become scarce and as the need to address environmental impact of non-renewable resources becomes critical. Thus, what is needed in the art are improved methods of producing fatty acids in bacteria, which is a renewable, relatively clean source of feedstock chemicals.

SUMMARY OF THE DISCLOSURE

The present invention establishes an in vivo method to improve the production of fatty acids by alleviating the reliance on the availability of NADPH, by supplementing or replacing NADPH-dependent enzymes with NADH-dependent enzymes.

Free fatty acids can be produced if one also adds an overexpressed TE gene, and the profile of fat lengths can be altered by changing TE specificity. If biodiesel if preferred, a gene that catalyzes ester formation can also be added, such as wax ester synthase/acyl-CoA-diacylglycerol acyltransferase (WS/DGAT) gene from the *Acinetobacter baylyi*. Alternatively, the free fats can be isolated and converted to esters by chemical reaction.

The bacteria can also be combined with cellulose enzymes having a signal for secretion. Such bacteria could then be grown on various cellulose-containing waste materials, and secrete fuels such as free fatty acids or fatty acid esters (biodiesel) into the medium.

FIG. 1 shows a simplified central aerobic metabolic pathway and the fatty acid synthesis pathway of $E.\ coli$, including the newly added NADH-dependent 3-oxoacyl-[acyl-carrier-protein] (ACP) reductase (underlined).

This invention represents a completely new approach to alleviate the potential NADPH availability bottle-neck by using a NAD$^+$ dependent 3-oxoacyl-ACP reductase to replace and/or augment the native NADP$^+$ dependent 3-oxoacyl-ACP. The NAD$^+$ dependent 3-oxoacyl-ACP reductase carries out the following reactions:

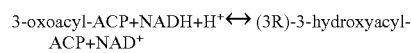

3-oxoacyl-ACP+NADH+H$^+$ ⟷ (3R)-3-hydroxyacyl-ACP+NAD$^+$

Or

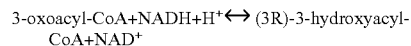

3-oxoacyl-CoA+NADH+H$^+$ ⟷ (3R)-3-hydroxyacyl-CoA+NAD$^+$

It is shown herein that the fatty acid production by engineered cells carrying a NAD$^+$ dependent 3-oxoacyl-ACP reductase gene is much more efficient, resulting in faster production rates, higher product yields and higher titers.

It is also expected that the concept of this disclosure can be applied to all organisms utilizing FASII for fatty acid synthesis, as it has been established that cells have higher concentration of NADH/NAD$^+$ than NADPH/NADP$^+$.

In one aspect of this disclosure, there is provided a genetically engineered organism with improved productivity of a product, preferably fatty acids and/or a product downstream of a fatty acid. The biosynthesis pathway of fatty acids has at least one $NADP^+$-dependent enzyme that catalyzes the synthesis of an intermediate product, such as 3-D-hydroxyacyl-ACP, and this rate limiting point is avoided by adding in an NADH-dependent enzyme instead.

The engineered organism can comprise a down-regulated or disrupted native $NADP^+$-dependent enzyme, but this isn't necessary, and the native enzyme can be left in place to take advantage of the available NADPH. An expressed or overexpressed $NAD^+$-dependent enzyme is added, wherein the $NAD^+$-dependent enzyme catalyzes the synthesis of the same intermediate product as the $NADP^+$-dependent enzyme.

The NADH-dependent enzyme can be selected from those known in the art, or an NADPH-dependent enzyme can be mutated such that it can use NADH instead, as there may only be one or a few amino acid changes needed.

NADH-dependent enzymes in fatty acid synthesis include:

EC 1.3.1.9—NADH-dependent enoyl-ACP reductase. The UniProt database provides more than 12,000 examples, a few of which are listed here:

| NADH-dependent enoyl-ACP reductases | Acc. No. | Gene |
|---|---|---|
| Acholeplasma laidlawi | A9NFJ2 | fabG2 |
| Arabidopsis thaliana (thale cress) | Q9SLA8 | MOD1 (ENR-A, ENR1) |
| Bacillus cereus | Q81GI3 | fabI |
| Bacillus subtilis | P54616 | fabI |
| Brassica napus (rape) | P80030 | |
| Burkholderia mallei | Q62L02 | BMA0885 |
| Caenorhabditis elegans (nematode) | F09E10.3 | dhs-25 |
| Ectocarpus siliculosus (brown algae) | D8LLF7 | Esi_0036_0144 |
| Escherichia coli | P0AEK4 | fabI |
| Galdieria sulphuraria (red algae) | M2WUK4 | Gasu_47760 |
| Helicobacter pylori | O24990 | fabI |
| Mycobacterium tuberculosis | Rv0242c I6Y778 | fabG4 |
| Mycobacterium tuberculosis | P9WGR1 | inhA |
| Oryza sativa (rice) | Q6H5J0 | Os09g0277800 |
| Pseudomonas aeruginosa | Q9ZFE4 | fabI |
| Saccharomyces cerevisiae (yeast) | P07149 | fasI |
| Salmonella typhimurium | P16657 | fabI |
| Streptococcus pneumonia | Q8DR17 | fabK |
| Toxoplasma gondii | Q6UCJ9 | ENR |
| Yersinia pestis | Q8Z9U1 | YPO4104 |

EC 1.1.1.212—NADH-dependent 3-oxoacyl [ACP]-reductase is less common, but examples are found in *Bacillus pumilus* (A8FCK1); *Persea Americana* and possibly *Euglena gracilis*. Similar proteins having at least 90% identity to A8FCK1 are shown:

| | |
|---|---|
| W8QVB6 | Bacillus pumilus (Bacillus mesentericus) |
| M5RHW9 | Bacillus stratosphericus LAMA 585 |
| A0A059NC82 | Bacillus safensis FO-36b |
| K2NZC4 | Bacillus sp. HYC-10 |
| A0A063YZZ3 | Bacillus pumilus ATCC 7061 |
| B4AEN4 | Bacillus sp. M 2-6 |
| I4V7T6 | Bacillus altitudinis 41KF2b |
| A0A059NRF1 | Bacillus pumilus (strain SAFR-032) |

Additionally, the FABG4 gene from *Mycobacterium tuberculosis* (Rv0242c) (Kegg) was classified as EC 1.1.1.100 (e.g., NADPH dependent) but is now known to use NADH. Another enzyme classified as EC 1.1.1.100 is the FabG2 (A9NFJ2) from *Acholeplasma laidlawii*, which is also able to use NADH. It is suspected that other NADPH classified enzymes may also be able to use NADH, and any potential enzyme can easily be screened by assay against NADH v. NADPH.

In another aspect of this disclosure, there is provided a method of increasing productivity of a product, preferably fatty acids or products made with fatty acids, in an engineered organism, wherein the biosynthesis pathway of the product has at least one $NADP^+$-dependent enzyme. The method comprises the following steps: a) optionally down-regulating or disrupting the $NADP^+$-dependent enzyme in the biosynthesis pathway of the product; b) introducing an exogenous $NAD^+$-dependent enzyme to replace or supplement the $NADP^+$-dependent enzyme in the biosynthesis pathway of the product; and c) growing these cells to make product and then isolating the product.

In other aspects of the disclosure, we provide an organism engineered to allow improved fatty acid production, comprising supplementing or replacing a native NADPH-dependent 3-oxoacyl-ACP reductase with a NADH-dependent 3-oxoacyl-ACP reductase or NADH-dependent 3-oxoacyl-CoA reductase, and wherein said organism has improved fatty acid production as compared to a comparable organism without said added NADH-dependent 3-oxoacyl-ACP reductase or NADH-dependent 3-oxoacyl-CoA reductase.

In another aspect, an *E. coli* is genetically engineered for improved fatty acid production, by replacing or supplementing a native NADPH-dependent 3-oxoacyl-ACP reductase gene with an exogenous $NAD^+$-dependent 3-oxoacyl-ACP reductase or an exogenous NADH-dependent 3-oxoacyl-coA reductase gene, wherein said *E. coli* makes more fatty acid than a comparable *E. coli* with only the native NADPH-dependent 3-oxoacyl-ACP reductase.

In another aspect, a FASII bacteria is genetically engineered for improved fatty acid production, said FASII bacteria comprising a disrupted native $NADP^+$-dependent 3-oxoacyl-ACP reductase gene replaced with an exogenous $NAD^+$-dependent 3-oxoacyl-ACP reductase gene, wherein said FASII bacteria makes more fatty acid than a comparable FASII bacteria with only the native $NADP^+$-dependent 3-oxoacyl-ACP reductase.

The exogenous NAD+-dependent 3-oxoacyl-ACP reductase gene can be from *Mycobacterium* or avocado or from nematode, or from the other sources described herein.

In another aspect, an FASII plant or algae is genetically engineered for improved fatty acid production, said FASII plant or algae comprising an exogenous $NAD^+$-dependent 3-oxoacyl-ACP reductase gene or $NAD^+$-dependent 3-oxoacyl-coA reductase gene wherein said FASII plant or algae makes more fatty acid than a comparable FASII plant or algae with only native $NADP^+$-dependent 3-oxoacyl-ACP reductase.

Another aspect of the disclosure provides a method of making fatty acids, comprising growing a bacterium with an added exogenous $NAD^+$-dependent 3-oxoacyl-ACP reductase gene or $NAD^+$-dependent 3-oxoacyl-coA reductase gene in a nutrient broth for a time sufficient to make fatty acids, and isolating said fatty acids.

Another aspect is a method of making C4-22 fatty acids (preferably C6-C14, most preferred about C8-C10) comprising growing a bacteria with an added exogenous NADH-dependent 3-oxoacyl-ACP reductase gene or NADH-dependent 3-oxoacyl-coA reductase gene in a nutrient broth for a time sufficient to make fatty acids, and isolating said fatty acids. Different chain lengths can be made by changing the specificity of the TE gene. Jing (2011) teaches a great number of TE genes (incorporated by reference herein in its entirety for all purposes), as well as their chain length specificities.

The organisms described herein can also comprise a down-regulated beta oxidation pathway to further increase fatty acid production, and/or can be modified to produce particular chain lengths of fatty acids.

The organisms described herein can also comprise an added TE gene, the specificity of which is tailored for the free fatty acids desired. US20140093921 (incorporated by reference in its entirety for all purposes) for example, teaches how to use added TE genes to make free fatty acids, and even teaches hybrid TE genes to make fats of the desired chain length. It also teaches combining the overexpressed TE with i) at least one protein from the tricarboxylic acid cycle is reduced, or ii) at least one protein from glycolysis is reduced, or both i) and ii) are reduced.

The TCA enzymes that can be reduced or inactivated include aconitase, isocitrate dehydrogenase, α-ketoglutarate dehydrogenase, succinyl-coA synthetase, succinic dehydrogenase, fumarase, malate dehydrogenase, and citrate synthase. In preferred embodiments the microorganism comprises inactivated succinyl-coA synthetase. In other embodiments, the organism is *E. coli* and the mutated TCA gene is the sucC gene, which encodes the succinyl-CoA synthetase beta subunit.

Glycolytic enzymes include hexokinase (aka glucokinase), phosphoglucose isomerase, phosphofructokinase, aldolase, triose phosphate isomerase, glyceraldehyde-3-phosphate dehydrogenase, phophoglycerate kinase, phophoglycerate mutate, enolase, pyruvate kinase, and the transport enzymes for glucose uptake, such as glucose phophotransferase (aka glucose permease). Glucokinase and glucose phophotransferase are particularly preferred. In other embodiments, the organism is *E. coli* and the mutated glycolytic gene is pstG or glk.

Exemplary SEQ are provided in Table A, but hundreds of examples of each gene/enzyme are available in GenBank, UniProt, and other databases:

TABLE A

Abbreviations and Definitions

| gene name | Definition (Protein name) | Exemplary UNIPROTKB Acc. No. |
|---|---|---|
| fabA | Gene that encodes beta-hydroxydecanoyl thioester dehydrase (protein = FabA) (EC: 5.3.3.14) | P0A6Q3 |
| fabB | Gene that encodes 3-oxoacyl-[acyl-carrier-protein] synthase (protein = FabB) | P0A953 |
| fadE | Gene that encodes acyl coenzyme A dehydrogenase (EC: 1.3.99.3) (FadE) | Q47146 |
| fabH | Gene that encodes 3-oxoacyl-[acyl-carrier-protein] synthase III (protein = FabH) (EC: 2.3.1.180) | P0A6R0 |
| fabR | Gene that encodes DNA-binding transcription repressor (protein = FabR) | P0ACU5 |
| fabZ | Gene that encodes a component of the complex 3R-hydroxymuristoyl acyl carrier protein (ACP) dehydratase (protein = FabZ) (EC: 4.2.1.59) | P0A6Q6 |
| fadD | Gene that encodes acyl-CoA synthetase (protein = FadD) (EC: 6.2.1.3) | P69451 |
| fadR | Gene that encodes DNA-binding transcriptional dual regulator of fatty acid metabolism (protein = FadR) | P0A8V6 |

TABLE A-continued

Abbreviations and Definitions

| gene name | Definition (Protein name) | Exemplary UNIPROTKB Acc. No. |
|---|---|---|
| sucC | Gene that encodes succinyl-CoA synthetase, beta subunit (protein = SucC) (EC: 6.2.1.5) | P0A836 |
| ptsG | Gene that encodes component of EIIGlc; enzyme II glc; Glucose phophotransferase enzyme IIBC(Glc); glucose permease (PtsG) (EC: 2.7.1.69) | P69786 |
| TE | Any gene encoding an acyl ACP thioesterase (TE), not an assigned gene name, but used herein. | See throughout. |
| ldhA | Gene encoding Lactate dehydrogenase (EC: 1.1.1.28) | NP_415898 (GenBank)I; D5D2D6 |
| pta | Gene encoding Phosphate acetyltransferase (EC: 2.7.2.1) | P0A9M8 |
| ackA | Gene encoding Acetate kinase, in an operon with pta in some species and often both deleted (EC 2.7.2.1) | P0A6A3 |
| udhA | Gene encoding transhydrogenase (UDH), aka sthA (EC: 1.6.1.1) | P27306 NP_418397.2 (GenBank), see also Q8ZA97 (*Shigella*); Q57H91 (*Salmonella*); Q66G61 (*Yersinia*), D5CGP9 (*Enterobacter*) among thousands of available species |
| pntAB | Gene encoding pntA (EC: 1.6.1.2) and PntB | P07001, BAA15342 (GenBank) P0AB67, YP_489865.1 (GenBank) |
| iclR | Gene encoding repressor of aceBA operon, regulation of the glyoxylate bypass operon (aceBAK), which encodes isocitrate lyase, malate synthase as well as isocitrate dehydrogenase kinase/phosphorylase. | P16528 |
| icdA | Gene encoding Isocitrate dehydrogenase [NADP] (EC: 1.1.1.42) | P08200 |
| acs | Gene encoding Acetyl-coenzyme A synthetase (EC: 6.2.1.1) | P27550 |

Another embodiment is combining the above with an overexpressed β-ketoacyl-acyl carrier protein synthase III gene with a greater substrate preference for propionyl-coA per US20140193867 (incorporated by reference herein in its entirety for all purposes), which teaches method of making odd chain free fats by using an overexpressed β-ketoacyl-acyl carrier protein synthase III gene with a greater substrate preference for propionyl-coA than acetyl-coA.

Another embodiment is combining the above with both long and short chain TE genes, which surprisingly results in more short chain fats. US20140212935 (incorporated by reference herein in its entirety for all purposes) teaches a method of making shorter chain fats by an overexpressed gene encoding a long chain (>C12) acyl-ACP thioesterases (long-TE) and an overexpressed gene encoding a short chain (≤C12) acyl-ACP thioesterases (short-TE).

Genotypes invented herein include one or more of the following:

NAD$^+$-dependent 3-oxoacyl-ACP reductase$^+$
NAD$^+$-dependent 3-oxoacyl-ACP reductase$^+$, TE$^+$ -continued FabG4⁺
FabG4⁺, TE⁺
FabG3⁺
FabG3⁺, TE⁺
FabG2⁺
FabG2⁺, TE⁺
FabG4⁺, TE⁺
NAD⁺-dependent 3-oxoacyl-ACP reductase⁺, TE⁺ plus one or more of fadD⁻, sth⁻ and pntAB⁻.
FabG4⁺, TE⁺ plus one or more of ΔfadD, Δsth, ΔpntAB Other genotypes that can be combined with any of the genotypes herein include:

ΔfadD, ΔsucC
ΔfadD, ΔfumAC and optional ΔsucC
ΔfadD, ΔgapA and optional ΔsucC
ΔfadD, ΔptsG and optional ΔsucC
ΔfadD, ΔpfkA and optional ΔsucC
ΔfadD, Δglk⁺ and optional ΔsucC
TE⁺ and fabD⁺
TE⁺ and udhA⁺
ΔsucC
ΔfumAC and optional ΔsucC
ΔgapA and optional ΔsucC
ΔptsG and optional ΔsucC
ΔpfkA and optional ΔsucC
Δglk and optional ΔsucC
NADP-kinase⁺
acc⁺ and/or fabD⁺ and/or udhA⁺ and/or NAD-kinase⁺ combined with any genotypes in this table
ΔldhA combined with any genotypes in this table
Δack or Δpta or Δack-pta combined with any genotypes in this table
ΔpoxB combined with any genotypes in this table
ΔfadE combined with any genotypes in this table
ΔiclR combined with any genotypes in this table Initial cloning experiments have proceeded in *E. coli* for convenience since most of the required genes are already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella, Streptococcus, Paracoccus, Methanosarcina*, and *Methylococcus*, or any of the completely sequenced bacterial species. Indeed, hundreds of bacterial genomes have been completely sequenced, and this information greatly simplifies both the generation of vectors encoding the needed genes, as well as the planning of a recombinant engineering protocol. Such species are listed along with links at http://en.wikipedia.org/wiki/List_of_sequenced_bacterial_genomes.

Additionally, yeast, such as *Saccharomyces*, are a common species used for microbial manufacturing, and many species can be successfully transformed. Indeed, yeast are already available that express recombinant thioesterases—one of the termination enzymes described herein—and the reverse beta oxidation pathway has also been achieved in yeast. Other species include but are not limited to *Candida, Aspergillus, Arxula adeninivorans, Candida boidinii, Hansenula polymorpha (Pichia angusta), Kluyveromyces lactis, Pichia pastoris*, and *Yarrowia lipolytica*, to name a few.

It is also possible to genetically modify many species of algae, including e.g., *Spirulina, Apergillus, Chlamydomonas, Laminaria japonica, Undaria pinnatifida, Porphyra, Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia, Haematococcus, Chaetoceros, Nannochloropsis, Skeletonema, Thalassiosira*, and *Laminaria japonica*, and the like. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See e.g., AddGene.org which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

The enzymes can be added to the genome or via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ expression plasmids hosting 3 or more ORFs for convenience, but it may be preferred to insert operons or individual genes into the genome for long term stability.

Still further improvements in yield can be had by reducing competing pathways, such as those pathways for making e.g., acetate, formate, ethanol, and lactate, and it is already well known in the art how to reduce or knockout these pathways. See e.g., the Rice patent portfolio by Ka-Yiu San and George Bennett (U.S. Pat. No. 7,569,380, U.S. Pat. No. 7,262,046, U.S. Pat. No. 8,962,272, U.S. Pat. No. 8,795,991) and patents by these inventors (U.S. Pat. No. 8,129,157 and U.S. Pat. No. 8,691,552) (each incorporated by reference herein in its entirety for all purposes). Many others have worked in this area as well.

Generally speaking we have referenced protein names herein and included EC numbers for accurate identification, but it is understood that a change in protein activity can of course be effected by changing the gene. This provides clarity since the gene nomenclature can be widely divergent in bacteria, but the proteins are defined by their activities and EC numbers.

Once an exemplary protein is obtained, e.g., in *E. coli*, which is completely sequenced and which is the workhorse of genetic engineering and bioproduction, many additional examples proteins of similar activity can be identified by BLAST search. Further, every protein record is linked to a gene record, making it easy to design expression or overexpression vectors. Many of the needed enzymes are already available in vectors, and can often be obtained from cell depositories or from the researchers who cloned them. But, if necessary, new clones can be prepared based on available sequence information using RT-PCR techniques. Thus, it should be easily possible to obtain all of the needed enzymes for overexpression.

Another way of finding suitable enzymes/proteins for use in the invention is to consider other enzymes with the same EC number, since these numbers are assigned based on the reactions performed by a given enzyme. An enzyme that thus be obtained, e.g., from AddGene or from the author of the work describing that enzyme, and tested for functionality as described herein. In addition, many sites provide lists of proteins that all catalyze the same reaction.

Understanding the inherent degeneracy of the genetic code allows one of ordinary skill in the art to design multiple nucleotides that encode the same amino acid sequence. NCBI provides codon usage databases for optimizing DNA sequences for protein expression in various species. Using such databases, a gene or cDNA may be "optimized" for expression in *E. coli*, or other bacterial species using the codon bias for the species in which the gene will be expressed.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250, and available through the NCBI website. The default parameters were used, except the filters were turned OFF.

The term "endogenous" or "native" means that a gene originated from the species in question, without regard to subspecies or strain, although that gene may be naturally or intentionally mutated, or placed under the control of a promoter that results in overexpression or controlled expression of said gene. Thus, genes from Clostridia would not be endogenous to *Escherichia*, but a plasmid expressing a gene from *E. coli* or would be considered to be endogenous to any genus of *Escherichia*, even though it may now be overexpressed.

"Expression vectors" are used in accordance with the art accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expressions vectors also exist.

As used herein, "inducible" means that gene expression can be controlled by the hand of man, by adding e.g., a ligand to induce expression from an inducible promoter. Exemplary inducible promoters include the lac operon, inducible by IPTG, the yeast AOX1 promoter inducible with methanol, the strong LAC4 promoter inducible with lactate, and the like. Low level of constitutive protein synthesis may occur even in expression vectors with tightly controlled promoters.

As used herein, an "integrated sequence" means the sequence has been integrated into the host genome, as opposed to being maintained on an expression vector. It will still be expressible, and preferably is inducible as well.

As used herein, the expressions "cell", "cell line" and "cell culture" are used interchangeably and all such designations include progeny. Thus, the words "cells" and similar designations include the primary subject cell and cultures derived therefrom without regard for the number of generation. It is also understood that all progeny may not be precisely identical in DNA content, due to deliberate or inadvertent mutations that arise after engineering is concluded. Mutant progeny that have the same function or biological activity as screened for in the originally transformed cell are included. Where distinct designations are intended, it will be clear from the context.

As used herein, reference to a "cell" is generally understood to include a culture of such cells, as the work described herein is done in cultures having $10^{9-15}$ cells.

As used herein, "growing" cells used it its art accepted manner, referring to exponential growth of a culture of cells, not the few cells that may not have completed their cell cycle at stationary phase or have not yet died in the death phase or after harvesting.

As used herein, "homolog" means an enzyme with at least 50% identity to one of the listed sequences and also having the same general catalytic activity. While higher identity (60%, 70%, 80%) and the like may be preferred, it is typical for bacterial sequences to diverge significantly (40-60%), yet still be identifiable as homologs, while mammalian species tend to diverge less (80-90%).

The terms "operably associated" or "operably linked," as used herein, refer to functionally coupled nucleic acid sequences.

As used herein, "engineered" means an organism being recombinantly modified to change its genetics in a particular way to achieve a particular result.

As used herein "recombinant" or "recombinant engineering" is relating to, derived from, or containing genetic material intentionally modified by the hand of man. In other words, the genetics were intentionally manipulated in some way.

By "metabolically modified" we refer to random mutagenesis and selective pressure to evolve an organism in a desired direction. Such procedures are often employed after a recombinant engineering step to further improve production of a desired product.

"Reduced activity" or "inactivation" or "down-regulated" is defined herein to be at least a 75% reduction in protein activity, as compared with an appropriate control species. Preferably, at least 80, 85, 90, 95% reduction in activity is attained, and in the most extreme embodiment, the activity is eliminated (100%). Proteins can be inactivated with inhibitors, by mutation, or by suppression of expression or translation, and the like.

The terms "disruption" as used herein, refer to cell strains in which the native gene or promoter is mutated, deleted, interrupted, or down regulated in such a way as to decrease the activity of the protein at least 90% over the wild type un-disrupted protein. A gene or protein can be completely (100%) reduced by knockout or removal of the entire genomic DNA sequence. A knockout mutant can be represented by the Δ symbol.

Use of a frame shift mutation, early stop codon, point mutations of critical residues, or deletions or insertions, and the like, can completely inactivate (100%) gene product by completely preventing transcription and/or translation of active protein.

"Overexpression" or "overexpressed" is defined herein to be at least 150% of protein activity as compared with an appropriate control species or as having expression of a gene not normally present in that host. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like. An overexpressed gene can be represented by the $^+$ symbol, e.g., PYC$^+$. In contrast, "expression" refers to normal levels of activity or better.

Acid and base forms of a molecule are used interchangeably herein, thus use of butyrate is intended to and does include butanoic acid.

NAD+ and NADH are used interchangeably herein, since the reactions involved convert one to the other. Likewise, NADP+ and NADPH are used interchangeably.

An "NAPDH-dependent" enzyme relies on NADPH as a cofactor, whereas an "NADH-dependent" enzyme uses NADH. Where an enzyme can use either, it is generally written as NAD(P)H.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as background mutations, nutrient media, buffers, and the like.

The following abbreviations are used herein:

| ABBREVIATION | TERM |
| --- | --- |
| FASII | Type II fatty acid synthase |
| ACP | acyl-carrier-protein |
| fadD | Fas-associated protein with death domain |
| sth | Cytoplasmic transhydrogenase |
| TE | Acyl-acyl carrier protein (ACP) thioesterase |
| FabG4 | an NAD+-dependent 3-oxoacyl-ACP reductase from M. tuberculosis (Rv0242c) |
| mt | M. tuberculosis |
| G1 | FabG4 |
| G2 | FabG4 with 16 N-terminal amino acid deletion |

Acyl-acyl carrier protein (ACP) thioesterase (TE) is an enzyme that terminates the intraplastidial fatty acid synthesis in plants by hydrolyzing the acyl-ACP intermediates and releasing free fatty acids to be incorporated into glycerolipids. These enzymes are classified in two families, FatA and FatB, which differ in amino acid sequence and substrate specificity. Generally speaking, the N terminal (aa 1-98) of any acyl-ACP thioesterases controls the substrate specificity of the enzyme, and it is known how to change substrate specificity by swapping amino terminal domains.

Many TE gene/proteins are known and can be added to bacteria for use in the invention (e.g., CAA52070, YP_003274948, ACY23055, AAB71729, BAB33929, to provide the accession numbers for a few of the thousands of such proteins available), although we have used plasmids encoded plant genes herein. Such genes can be added by plasmid or other vector, or can be integrated directly into the genome.

Other acyl TE's include *Umbellularia californica* (AAC49001), *Cinnamomum camphora* (Q39473), *Umbellularia californica* fatty acyl-ACP thioesterase (Q41635), *Myristica fragrans* (AAB71729), *Myristica fragrans* (AAB71730), *Elaeis guineensis* (ABD83939), *Elaeis guineensis* (AAD42220), *Populus tomentosa* (ABC47311), *Arabidopsis thaliana* (NP_172327), *Arabidopsis thaliana* (CAA85387), *Arabidopsis thaliana* (CAA85388), *Gossypium hirsutum* (Q9SQI3), *Cuphea lanceolata* (CAA54060), *Cuphea hookeriana* (AAC72882), *Cuphea calophylla* subsp. *mesostemon* (ABB71581), *Cuphea lanceolata* (CAC19933), *Elaeis guineensis* (AAL15645), *Cuphea hookeriana* (Q39513), *Gossypium hirsutum* (AAD01982), *Vitis vinifera* (CAN81819), *Garcinia mangostana* (AAB51525), *Brassica juncea* (ABI18986), *Madhuca longifolia* (AAX51637), *Brassica napus* (ABH11710), *Oryza sativa* (indica cultivar-group) (EAY86877), *Oryza sativa* (*japonica* cultivar-group) (NP-001068400), *Oryza sativa* (indica cultivar-group) (EAY99617), and *Cuphea hookeriana* (AAC49269).

In some embodiments, at least one TE gene is from a plant, for example overexpressed TE from *Ricinus communis* (XP_002515564.1), *Jatropha curcas* (ABU96744.1), *Diploknema butyracea* (AAX51636.1), *Cuphea palustris* (AAC49180.1), or *Gossypium hirsutum* (AAF02215.1 or AF076535.1), or an overexpressed hybrid TE comprising different thioesterase domains operably fused together (see WO2011116279, all sequences expressly incorporated by reference herein). It also teaches acidifying the medium to increase production of fatty acids. Preferably, the hybrid thioesterase includes an amino terminal region (~aa 1-98 controls substrate specificity) of the acyl-ACP thioesterase from *Ricinus communis* or a 70, 80, 90 or 95% homolog thereto, or any TE with the desired substrate specificity, operably coupled to the remaining portion of the thioesterase from another species. In such manner, enzyme specificity can be tailored for the use in question.

A great number of TE proteins were characterized by Jing, and some of his results reproduced here:

| Kingdom | Subfamily | Acc No./Name | Organism | Rationale for synthesis[a] | Total Fa[b] (nmol/mL) |
| --- | --- | --- | --- | --- | --- |
| Planta | A | AAC49179[c,d] | Cuphea palustris | A (Bimodal specificity for C8 and C10 substrates) [1] | 708 ± 45 |
| | | AAB71731 | Ulmus Americana | A (Broad specificity; highest activity on C10 and C16) [13] | 1098 ± 62 |
| | | AAG43857 | Iris germanica | B | 261 ± 20 |
| | | AAG43858 | Iris germanica | B | 14.8 ± 4.6 |
| | | EER87824 | Sorghum bicolor | B (Member of a Subfamily A Poeceae TE cluster) | 126 ± 13 |
| | | EER88593 | Sorghum bicolor | B (Member of a Subfamily A Poeceae TE cluster) | 90.7 ± 8.0 |
| | | CnFatB1 | Cocos nucifera | C | 130 ± 12 |
| | | CnFatB2 | Cocos nucifera | C | 572 ± 32 |
| | | CnFatB3 | Cocos nucifera | C | 200 ± 11 |
| | | CvFatB1 | Cuphea viscosissima | C | 79.2 ± 9.7 |
| | | CvFatB2 | Cuphea viscosissima | C | 249 ± 9 |
| | | CvFatB3 | Cuphea viscosissima | C | 18.9 ± 2.1 |
| | | AAD42220 | Elaeis guineensis | C | 36.7 ± 3.8 |

| Kingdom | Subfamily | Acc No./Name | Organism | Rationale for synthesis[a] | Total Fa[b] (nmol/mL) |
|---|---|---|---|---|---|
| | B | EDQ65090 | *Physcomitrella patens* | B (Member of novel plant subfamily | 380 ± 29 |
| | | EER96252 | *Sorghum bicolor* | B (Member of novel plant subfamily | 175 ± 11 |
| | | EES11622 | *Sorghum bicolor* | B (Member of novel plant subfamily | 9.43 ± 2.03 |
| | D | EEH52851 | *Micromonas pusilla* | B | 16.3 ± 1.6 |
| Bacteria | E | ACL08376 | *Desulfovibrio vulgaris* | D (Medium-chain linear, branched, and hydroxy fatty acids) [29] | 330 ± 9 |
| | F | CAH09236 | *Bacteroides fragilis* | D (Hydroxy fatty acids) [29] | 215 ± 6 |
| | | ABR43801 | *Parabacteroides distasonis* | D (Branched and branched hydroxy fatty acids) [30] | 70.3 ± 4.4 |
| | | AAO77182[e] | *Bacteroides thetaiotaomicron* | D (Anteiso-branched and hydroxy fatty acids) [29] | 60.4 ± 2.9 |
| | G | ABG82470 | *Clostridium perfringens* | D (Medium-chain fatty acids) [31] | 72.0 ± 9.5 |
| | H | EEG55387 | *Clostridium asparagiforme* | B | 25.9 ± 4.2 |
| | | EET61113 | *Bryantella formatexigens* | B | 381 ± 3 |
| | I | EDV77528 | *Geobacillus* sp. | D (Iso-branched fatty acids) [32] | 64.9 ± 12.0 |
| | J | BAH81730 | *Streptococcus dysgalactiae* | D (Medium-chain and cyclic propane ring fatty acids) [29] | 623 ± 14 |
| | | ABJ63754 | *Lactobacillus brevis* | D (Medium-chain and cyclic propane ring fatty acids) [33] | 710 ± 10 |
| | | CAD63310[e] | *Lactobacillus plantarum* | D (Medium-chain 3'-hydroxy fatty acids) [33, 34] | 436 ± 10 |
| | Non-grouped | EEI82564 | *Anaerococcus tetradius* | D (Organism produces butyric acid) [35] | 1381 ± 146 |
| | | CAE80300 | *Bdellovibrio bacteriovorus* | D (Straight-chain odd-numbered fatty acids) [29] | 333 ± 18 |
| | | ABN54268 | *Clostridium thermocellum* | D (Branched-chain fatty acids) [29] | 97.7 ± 3.2 |

[a]A: Functionally characterized TEs; B: TE does not group near characterized TEs and/or no organism lipid profile information is available; C: TEs cloned from organisms known to produce MCFAs; D: Organism's lipid profile used and predominant fatty acid constituents identified in the organism are listed in parentheses.
[b]The data are represented as mean ± standard error (n = 4).
[c]All but the three *C. nucifera* sequences were codon-optimized for expression in *E. coli*.
[d]Transit peptides were removed from all plant sequences.
[e]Acyl-ACP TEs with known crystal structures.
TEs were expressed in *E. coli* K27, and free fatty acids (FAs) that accumulated in the medium were analyzed by GC-MS.

Thus it can be seen that hundreds of such TE proteins have been used, and are readily available for overexpression uses in the claimed microbes or bacteria.

The invention includes one or more of the following embodiments, in any combination:

An engineered microbe with improved productivity of a product, wherein the biosynthesis pathway of said product has at least one $NADP^+$-dependent enzyme, said engineered microbe comprising:
an $NADP^+$-dependent enzyme that catalyzes the synthesis of an intermediate or a product; and
an overexpressed $NAD^+$-dependent enzyme that replaces or supplements said $NADP^+$-dependent enzyme;
wherein said $NAD^+$-dependent enzyme catalyzes the synthesis of said intermediate or said product.
An engineered microbe wherein said engineered microbe is a type II fatty acid synthesis (FASII) microbe that comprises one or more acyl-ACP thioesterases (TE).
An engineered microbe wherein said engineered microbe is a type II fatty acid synthesis (FASII) microbe and said product is fatty acids or fatty acid derivatives.
An engineered microbe wherein said product is free fatty acids or derivatives thereof, such as hydroxyl fatty acids or dicarboxylic acids.
An engineered microbe said microbe further comprising reduced activity of one or enzymes selected from beta-oxidation cycle enzymes, acetate synthesis enzymes, lactate synthesis enzymes, formate synthesis enzymes ethanol synthesis enzymes, glycolytic enzymes or tricarboxylic acid (TCA) cycle enzymes.
AN engineered microbe wherein said overexpressed $NAD^+$-dependent enzyme is full length or partial length $NAD^+$-dependent 3-oxoacyl-ACP reductase or $NAD^+$-dependent 3-oxoacyl-CoA reductase.
An engineered microbe wherein said overexpressed $NAD^+$-dependent enzyme is full length or partial length $NAD^+$-dependent 3-oxoacyl-ACP reductase or $NAD^+$-dependent 3-oxoacyl-CoA reductase.
An engineered microbe where said partial length $NAD^+$-dependent 3-oxoacyl-ACP reductase or $NAD^+$-dependent 3-oxoacyl-CoA reductase has omission of the first 16 amino acids of the full length enzyme.
An engineered microbe wherein said NAD+-dependent 3-oxoacyl-ACP reductase or $NAD^+$-dependent 3-oxoacyl-CoA reductase is from *Mycobacterium tuberculosis*.
An engineered microbe wherein said NAD+-dependent 3-oxoacyl-ACP reductase is Rv0242c.
An engineered microbe said engineered microbe further comprising at least one downregulated or disrupted gene selected from one or more of fadD, sth and pntAB.

-continued

A genetically engineered bacteria comprising an exogenous overexpressed NAD$^+$-dependent 3-oxoacyl-ACP reductase and one or more overexpressed acyl-ACP thioesterases (TE), wherein said E. coli makes more fatty acid than a comparable E. coli with only a native NADP$^+$-dependent 3-oxoacyl-ACP reductase.

A genetically engineered Escherichia comprising an exogenous overexpressed NAD$^+$-dependent 3-oxoacyl-ACP reductase and one or more overexpressed acyl-ACP thioesterases (TE), wherein said E. coli makes more fatty acid than a comparable E. coli with only a native NADP$^+$-dependent 3-oxoacyl-ACP reductase.

A microbe as described herein wherein the microbe is a bacteria or algae, preferably Escherichia, Bacillus, Lactobacillus, Streptococcus, Staphylococcus, Haemophilus, and the like or cyanobacteria, green algae (Chlorophyta), red algae (Rhodophyta) or brown algae (Phaeophyta).

A microbe as described herein further having i) at least one protein from the tricarboxylic acid cycle is reduced, or ii) at least one protein from glycolysis is reduced, or both i) and ii) are reduced.

A microbe as described herein wherein said at least one protein from the tricarboxylic acid cycle is selected from the group consisting of aconitase, isocitrate dehydrogenase, α-ketoglutarate dehydrogenase, succinyl-coA synthetase, succinic dehydrogenase, fumarase, malate dehydrogenase, and citrate synthase.

A microbe as described herein wherein said at least one protein from the tricarboxylic acid cycle is succinyl-CoA synthetase.

A microbe as described herein wherein said at least one protein from glycolysis is selected from glucokinase, phosphoglucose isomerase, phosphofructokinase, aldolase, triose phosphate isomerase, glyceraldehyde-3-phosphate dehydrogenase, phophoglycerate kinase, phophoglycerate mutate, enolase, pyruvate kinase, and glucose phophotransferase.

A microbe as described herein wherein said at least one gene from glycolysis is glucokinase or glucose phophotransferase.

A microbe as described herein further comprising at least one further modification selected from the group consisting of i) overexpressed malonyl coenzyme A-acyl carrier protein transacylase, ii) overexpressed transhydrogenase, iii) moderately overexpressed acetyl-CoA carboxylase, iv) overexpressed NAD kinase and v) reduced activity of endogenous fatty acyl-CoA synthetase.

A microbe as described herein wherein said transhydrogenase is a soluble pyridine nucleotide transhydrogenase.

A microbe as described herein which makes 30%, 50%, 75% OR 100% more fatty acid than a comparable microbe without the added NADH-dependent 3-oxoacyl-ACP reductase An FASII microbe genetically engineered for improved fatty acid production, said FASII microbe comprising a native NADP$^+$-dependent 3-oxoacyl-ACP reductase gene replaced or supplemented with an exogenous NAD$^+$-dependent 3-oxoacyl-ACP reductase gene, plus one or more overexpressed TE enzymes, wherein said FASII microbe makes more fatty acid than a comparable FASII microbe with only the native NADP$^+$-dependent 3-oxoacyl-ACP reductase.

A microbe further comprising reduced activity of one or enzymes selected from beta-oxidation cycle enzymes, acetate synthesis enzymes, lactate synthesis enzymes, formate synthesis enzymes ethanol synthesis enzymes, glycolytic enzymes or tricarboxylic acid (TCA) cycle enzymes.

A microbe further comprising at least one down-regulated or disrupted gene selected from the group consisting of: fadD, fadE and the native NADP$^+$-dependent 3-oxoacyl-ACP reductase.

A microbe further comprising at least one up-regulated gene selected from the group consisting of: sth, pntAB and NADK.

A method of making fatty acids, comprising growing a Type II FAS microbe with an added exogenous NAD$^+$-dependent 3-oxoacyl-ACP reductase gene or NAD$^+$-dependent 3-oxoacyl-coA reductase gene and an overexpressed TE enzyme in a nutrient broth for a time sufficient to make fatty acids, and isolating said fatty acids.

The method as described, said microbe including one or more of the modifications described herein.

BRIEF DESCRIPTION OF THE DRAWINGS

FIG. 1C provides each of the enzymatic reactions used in fatty acid synthesis of a FASII microbe, the two bolded enzymes using NADPH and being replaced or supplemented herein by an NADH-dependent enzyme.

FIG. 3A is a schematic diagram of the plasmid construct pXZ18G2 that carries an acyl-ACP thioesterase from Ricinus communis (accession no.: XM002515518) and a NAD+-dependent 3-oxoacyl-ACP reductase from Mycobacterium tuberculosis (accession no.: Rv0242c). Abbreviations: RBS, ribosomal binding site; rcTE, acyl-ACP thioesterase from R. communis; MtG2, a NAD$^+$-dependent 3-oxoacyl-ACP reductase (FabG4) from M. tuberculosis with an omission of the first 16 amino acids; lacI, regulator gene of trc promoter system; AmpR, ampicillin resistant gene; T1 terminator and T2 terminator, transcriptional terminator of rrnB; pBR322 origin, origin of replication.

FIG. 4: SEQ ID NO: 1 (XM002515518) rice TE.

FIG. 5: SEQ ID NO:2 (Rv0242c) *Mycobacterium* FabG4.

FIG. 6: SEQ ID NO:3 (truncated Rv0242c) *Mycobacterium* truncated FabG4.

FIG. 7: Simplified overview of the metabolites and representative pathways in microalgal lipid biosynthesis.

FIG. 12A-C: Constructs for generating anti-sense RNA against FabG without loop design. FIG. 12A: AS1; FIG. 12B: AS2; FIG. 12C: AS3.

FIG. 13A-C: Constructs for generating anti-sense RNA against FabG with loop design. FIG. 13A: AS1-looped; FIG. 13B: AS2-looped; FIG. 13C: AS3-looped.

DETAILED DESCRIPTION

This disclosure provides the inventive concept of replacing or supplementing the NADP+-dependent enzyme in a type II fatty acid synthesis pathway with an NAD+-dependent enzyme so as to take advantage of the higher concentration of NADH/NAD$^+$ in cells. In *E. coli*, as in many species, the 3-oxoacyl-ACP reductase is NADPH-dependent, and is thus rate limiting, and adding an NADH-dependant reductase alleviates this bottleneck, allowing more fats to be made.

To demonstrate the concept, we used previously constructed host strain *E. coli* strain, ML103 (MG1655, ΔfadD) for fatty acid production with a deleted long-chain fatty acyl coenzyme A synthase gene fadD. The ΔfadD is not an essential component of the invention, although it does improve fatty acid accumulation. FadD is the first step in the fatty acid beta-oxidation pathway. It activates the fatty acid to acyl-CoA before going into the beta-oxidation cycle, thus its deletion helps to conserve the fatty acids that are made. However, any enzyme in the beta-oxidation pathway can provide similar effects if reduced or knocked out.

The base strain also contained a thioesterase (TE) gene from *Ricinus communis*, which functions to release free fats from the ACP thus allow increased levels of free fatty acids to accumulate.

TE expression of some kind is needed to allow free fatty acid production. The host's native TE (such as TesA and TesB) is capable of providing some activity, but we have shown that overexpression of either endogenous or exogenous TE significantly improves free fatty acids levels. Furthermore, by tailoring the TE gene used, we are able to influence the length of the free fatty acids produced.

Figure 2:
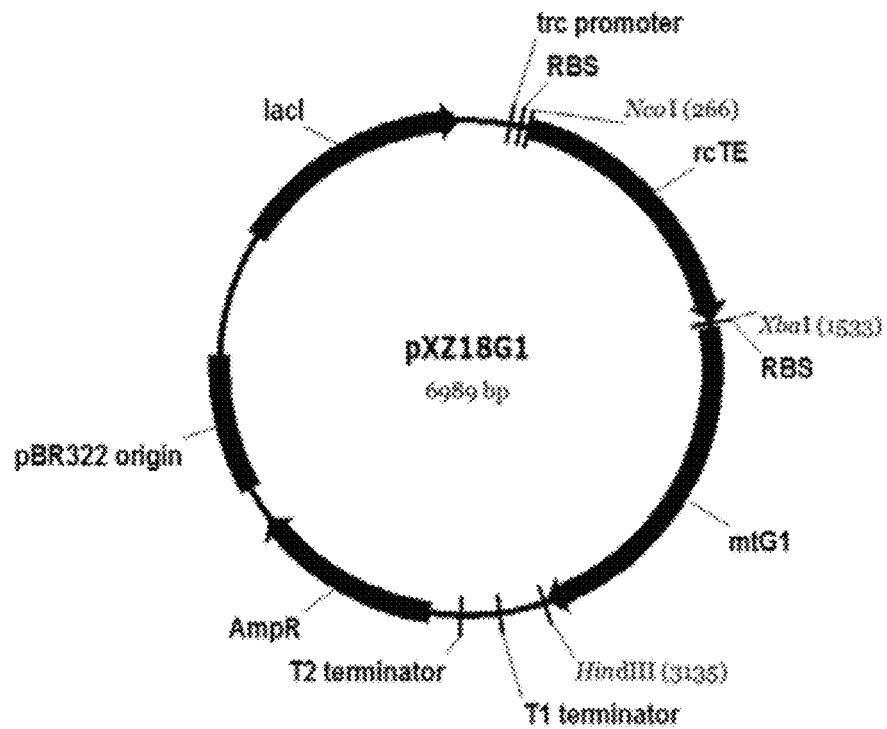
FIG. 2 is the schematic diagram of the plasmid construct pXZ18G1 that carries an acyl-ACP thioesterase from Ricinus communis (accession no.: XM002515518) and a NAD$^+$-dependent 3-oxoacyl-ACP reductase from Mycobacterium tuberculosis (accession no.: Rv0242c). Abbreviations: RBS, ribosomal binding site; rcTE, acyl-ACP thioesterase from R. communis; MtG1, an NAD$^+$-dependent 3-oxoacyl-ACP reductase (FabG4) from M. tuberculosis; lacI, regulator gene of trc promoter system; AmpR, ampicillin resistant gene; T1 terminator and T2 terminator, transcriptional terminator of rrnB; pBR322 origin, origin of replication.

A plasmid carrying an acyl-ACP thioesterase from *Ricinus communis* (Acc no.: XM002515518) (Zhang et al., 2011) and a NAD$^+$ dependent 3-oxoacyl-ACP reductase from *Mycobacterium tuberculosis* (Acc. no.: Rv0242c) is used as an example. Two versions, one with the full length reductase (named G1) and the other one with an omission of the first 16 amino acids (named G2) of the 3-oxoacyl-ACP reductase were tested, because the first 16 amino acids were found to hinder the solubility of the recombinant protein (Dutta et al, 2011). The schematics of the plasmid constructs pXZ18G1 and pXZ18G2 are shown in FIG. 2 and FIG. 3, respectively.

By replacing or supplementing NADP$^+$-dependent 3-oxoacyl-ACP reductase with NAD$^+$-dependent 3-oxoacyl-ACP reductase, the higher availability of NAD$^+$ in the organism will facilitate synthesis of fatty acids and result in higher yield thereof, especially long-chain fatty acid of 14 or more carbons. This significantly increases the efficiency of fatty acid production and reduces the cost thereof.

LB medium supplemented with approximately 15 g/L glycerol as a carbon source and 100 mg/L ampicillin for selection were used for culturing cells. Isopropyl-β-D-thiogalactopyranoside (IPTG) was added to the medium to a final concentration of 200 μM, thus inducing the expression of acyl-ACP thioesterase and NAD$^+$ dependent 3-oxoacyl-ACP reductase.

A single colony of strain (ML103-18 (control), ML103-18G1 (NADH-dependent enzyme) or ML103-18G2 (truncated NADH-dependent enzyme) was inoculated into 5 ml of Luria-Bertani (LB) and incubated in an orbital shaker operated at 250 rpm at 30° C. overnight. The pre-culture was inoculated into a flask containing 50 mL of the culture medium with 1% (v/v) inoculum. The culture medium contained 50 ml LB and about 15 g/L of glycerol.

Shake flask experiments were performed at 30° C. with shaking at 250 rpm. Samples were taken at four specific time points (0, 24, 48 and 72h) to quantify the fatty acids produced and glycerol consumed. All experiments were carried out in triplicates. The results are shown in Tables 1 and 2.

TABLE 1

Percentage improvement of fatty acid production and yield using a NAD+ dependent 3-oxoacyl-ACP reductase at 24, 48 and 72 hours. Values shown are averages of triplicates

| Strain | Relevant genotype | Time | Concentrations of free fatty acid (g/L) | | | | | Yield (g fatty acid/ g glycerol) | FFA % improvement | yield % improvement |
|---|---|---|---|---|---|---|---|---|---|---|
| | | | C14 | C16 | C16:1 | C18 | Total | | | |
| ML103-18 | ΔfadD, rcTE$^+$ | 24 h | 0.651 | 0.622 | 0.368 | 0.063 | 1.704 | 0.169 | — | — |
| ML103-18G1 | ΔfadD, rcTE$^+$ G1$^+$ | | 0.947 | 0.327 | 0.763 | 0.040 | 2.077 | 0.211 | 21.91 | 24.82 |
| ML103-18G2 | ΔfadD, rcTE$^+$ G2$^+$ | | 1.071 | 0.337 | 0.719 | 0.030 | 2.157 | 0.209 | 26.57 | 23.58 |
| ML103-18 | ΔfadD, rcTE$^+$ | 48 h | 0.850 | 0.733 | 0.383 | 0.063 | 2.030 | 0.146 | — | — |
| ML103-18G1 | ΔfadD, rcTE$^+$ G1$^+$ | | 1.346 | 0.399 | 0.946 | 0.043 | 2.733 | 0.194 | 34.68 | 32.41 |
| ML103-18G2 | ΔfadD, rcTE$^+$ G2$^+$ | | 1.323 | 0.376 | 0.796 | 0.031 | 2.526 | 0.203 | 24.46 | 38.57 |
| ML103-18 | ΔfadD, rcTE$^+$ | 72 h | 0.957 | 0.792 | 0.464 | 0.064 | 2.276 | 0.142 | — | — |
| ML103-18G1 | ΔfadD, rcTE$^+$ G1$^+$ | | 1.548 | 0.449 | 1.089 | 0.045 | 3.130 | 0.195 | 37.51 | 37.68 |
| ML103-18G2 | ΔfadD, rcTE$^+$ G2$^+$ | | 1.609 | 0.433 | 0.946 | 0.032 | 3.020 | 0.194 | 32.67 | 36.81 | rcTE$^+$: overexpression of acyl-ACP thioesterase from *Ricinus communis*;
G1$^+$: overexpression of a NAD$^+$ dependent 3-oxoacyl-ACP reductase from *M. tuberculosis*
G2$^+$: overexpression of a 16 aa truncant of the NAD$^+$ dependent 3-oxoacyl-ACP reductase from *M. tuberculosis*

TABLE 2

Fatty acid distribution comparison (derived from Table 1)

| Strain | Relevant genotype | Time | Fatty acid distribution (% of total free fatty acid) | | | | % increase C14 | % increase in % C14 |
|---|---|---|---|---|---|---|---|---|
| | | | C14 | C16 | C16:1 | C18 | | |
| ML103-18 | ΔfadD, rcTE$^+$ | 24 h | 38.218 | 36.520 | 21.577 | 3.685 | — | — |
| ML103-18G1 | ΔfadD, rcTE$^+$ G1$^+$ | | 45.581 | 15.725 | 36.751 | 1.943 | 45.390 | 19.265 |
| ML103-18G2 | ΔfadD, rcTE$^+$ G2$^+$ | | 49.640 | 15.646 | 33.340 | 1.374 | 64.399 | 29.886 |
| ML103-18 | ΔfadD, rcTE$^+$ | 48 h | 41.875 | 36.137 | 18.894 | 3.094 | — | — |
| ML103-18G1 | ΔfadD, rcTE$^+$ G1$^+$ | | 49.227 | 14.600 | 34.605 | 1.568 | 58.321 | 17.556 |
| ML103-18G2 | ΔfadD, rcTE$^+$ G2$^+$ | | 52.394 | 14.876 | 31.508 | 1.223 | 55.717 | 25.118 |
| ML103-18 | ΔfadD, rcTE$^+$ | 72 h | 42.022 | 34.814 | 20.366 | 2.798 | — | — |
| ML103-18G1 | ΔfadD, rcTE$^+$ G1$^+$ | | 49.451 | 14.341 | 34.780 | 1.428 | 61.814 | 17.678 |
| ML103-18G2 | ΔfadD, rcTE$^+$ G2$^+$ | | 53.273 | 14.336 | 31.337 | 1.054 | 68.191 | 26.772 | rcTE$^+$: overexpression of acyl-ACP thioesterase from *Ricinus communis*;
G1$^+$: overexpression of a NAD$^+$ dependent 3-oxoacyl-ACP reductase from *M. tuberculosis*
G2$^+$: overexpression of a 16 aa truncant of a NAD$^+$ dependent 3-oxoacyl-ACP reductase from *M. tuberculosis*

In summary, as shown in Table 1, both NAD$^+$ dependent 3-oxoacyl-ACP reductase carrying strains, ML103-18G1 and ML103-18G2, produced more fatty acids than that of the control strain ML103-18 (Table 1). At 72 hours, the ML103-18G1 and ML103-18G1 strains accumulated more than 34% and 32% of free fatty acids than that of the control strain ML103-18, respectively (Table 1). In addition, both NAD$^+$ dependent 3-oxoacyl-ACP reductase-carrying strains, ML103-18G1 and ML103-18G2, gave higher yields than that of the control strain ML103-18, more than 35% at 72 hours (Table 1).

Both NAD$^+$ dependent 3-oxoacyl-ACP reductase-carrying strains, ML103-18G1 and ML103-18G2, also showed changes in the free fatty acid distribution as compared to that of the control strain ML103-18 (Table 2). The ML103-18G1 and ML103-18G2 strains accumulated more than 61% and 68% of C14 free fatty acids than that of the control strain ML103-18, respectively (Table 2), but this is due to the substrate specificity of the added TE gene. Of course, the exit points can be modified by tailoring the exit point for the fatty acid elongation cycle (see e.g., WO2013096665). Thus, by changing the added TE gene, one can influence the fatty acid length.

The ability of the NAD$^+$ dependent 3-oxoacyl-ACP reductase to improve free fatty acid production in two pyridine nucleotide transhydrogenase mutant strains was also examined. The pyridine nucleotide transhydrogenases normally function to reoxidize NADPH, according to the following:

EC Number: 1.6.1.2/1.6.1.3
NAD$^+$+NADPH<=>NADP$^+$+NADH

Thus, deleting these would prevent the conversion of NADH to NADPH.

A strain WLK09 with the cytoplasmic transhydrogenase (sth) deactivated and the other strain WLK310 with the membrane bound transhydrogenase (pntB) deactivated were used. Both strains also have the beta-oxidation pathway blocked by deleting the fadD gene to prevent the degradation of fatty acids produced in vivo.

LB medium supplemented with approximately 15 g/L glycerol as a carbon source and 100 mg/L ampicillin for selection were used for culturing cells. IPTG was added to a final concentration of 200 μM, thus inducing the expression of the added genes.

A single colony of each strain (ML309-18, ML309-18G1 & ML309-18G2 or ML310-18, ML310-18G1 or ML310-18G2) was inoculated into 5 ml of Luria-Bertani (LB) and treated as above. The results are shown in Tables 3 and 4 below.

TABLE 3

Effect of NAD+ dependent 3-oxoacyl-ACP reductase in a transhydrogenase mutant host

| Strain | Relevant genotype | Time | Concentrations of free fatty acid (g/L) | | | | | Yield (g fatty acid/ g glycerol) | FFA % improvement | yield % improvement |
|---|---|---|---|---|---|---|---|---|---|---|
| | | | C14 | C16 | C16:1 | C18 | Total | | | |
| WLK309-18 | ΔfadD, Δsth, rcTE+ | 24 h | 0.150 | 0.157 | 0.197 | 0.023 | 0.527 | 0.145 | | |
| WLK309-18G2 | ΔfadD, Δsth, rcTE+ | | 0.375 | 0.157 | 0.327 | 0.011 | 0.871 | 0.148 | 65.24 | 1.87 |
| WLK310-18 | ΔfadD, ΔpntAB, rcTE+ G2+ | | 0.204 | 0.297 | 0.539 | 0.123 | 1.163 | 0.123 | | |
| WLK310-18G2 | ΔfadD, ΔpntAB, rcTE+ G2+ | | 0.568 | 0.272 | 0.786 | 0.050 | 1.676 | 0.160 | 44.09 | 30.12 |
| WLK309-18 | ΔfadD, Δsth, rcTE+ | 48 h | 0.707 | 0.550 | 0.581 | 0.069 | 1.907 | 0.162 | | |
| WLK309-18G2 | ΔfadD, Δsth, rcTE+ | | 1.279 | 0.356 | 0.674 | 0.018 | 2.326 | 0.173 | 21.98 | 7.10 |
| WLK310-18 | ΔfadD, ΔpntAB, rcTE+ G2+ | | 0.211 | 0.317 | 0.552 | 0.149 | 1.230 | 0.080 | | |
| WLK310-18G2 | ΔfadD, ΔpntAB, rcTE+ G2+ | | 0.582 | 0.279 | 0.793 | 0.067 | 1.720 | 0.111 | 39.84 | 39.55 |
| WLK309-18 | ΔfadD, Δsth, rcTE+ | 72 h | 0.916 | 0.621 | 0.619 | 0.080 | 2.237 | 0.158 | — | — |
| WLK309-18G2 | ΔfadD, Δsth, rcTE+ | | 1.592 | 0.421 | 0.790 | 0.023 | 2.825 | 0.180 | 26.33 | 13.83 |
| WLK310-18 | ΔfadD, ΔpntAB, rcTE+ G2+ | | 0.233 | 0.360 | 0.623 | 0.168 | 1.384 | 0.089 | — | — |
| WLK310-18G2 | ΔfadD, ΔpntAB, rcTE+ G2+ | | 0.618 | 0.288 | 0.844 | 0.074 | 1.824 | 0.118 | 31.76 | 32.72 | rcTE+: overexpression of acyl-ACP thioesterase from *Ricinus communis*;
G1+: overexpression of a NAD+ dependent 3-oxoacyl-ACP reductase from *M. tuberculosis*
G2+: overexpression of a derivative of a NAD+ dependent 3-oxoacyl-ACP reductase from *M. tuberculosis*
ΔpntAB = deactivation of the membrane bounded transhydrogenase
Δsth = deactivation of the soluble transhydrogenase

TABLE 4

Fatty Acid distribution Comparison (derived from Table 3)

| Strain | Relevant genotype | Time | Fatty acid distribution (% of total free fatty acid) | | | | % increase C14 | % increase in % C14 |
|---|---|---|---|---|---|---|---|---|
| | | | C14 | C16 | C16:1 | C18 | | |
| WLK309-18 | ΔfadD, Δsth, rcTE+ | 24 h | 0.284 | 0.298 | 0.374 | 0.044 | | |
| WLK309-18G2 | ΔfadD, Δsth, rcTE+ G1+ | | 0.430 | 0.180 | 0.376 | 0.013 | 150.71 | 51.72 |
| WLK310-18 | ΔfadD, ΔpntAB, rcTE+ G2+ | | 0.176 | 0.255 | 0.463 | 0.106 | | |
| WLK310-18G2 | ΔfadD, ΔpntAB, rcTE+ G2+ | | 0.339 | 0.162 | 0.469 | 0.030 | 177.82 | 92.82 |
| WLK309-18 | ΔfadD, Δsth, rcTE+ | 48 h | 0.371 | 0.288 | 0.305 | 0.036 | | |
| WLK309-18G2 | ΔfadD, Δsth, rcTE+ G1+ | | 0.550 | 0.153 | 0.290 | 0.008 | 80.85 | 48.26 |
| WLK310-18 | ΔfadD, ΔpntAB, rcTE+ G2+ | | 0.172 | 0.258 | 0.449 | 0.121 | | |
| WLK310-18G2 | ΔfadD, ΔpntAB, rcTE+ G2+ | | 0.338 | 0.162 | 0.461 | 0.039 | 175.57 | 97.06 |
| WLK309-18 | ΔfadD, Δsth, rcTE+ | 72 h | 0.409 | 0.278 | 0.277 | 0.036 | | |
| WLK309-18G2 | ΔfadD, Δsth, rcTE+ G1+ | | 0.563 | 0.149 | 0.279 | 0.008 | 73.81 | 37.59 |

TABLE 4-continued

Fatty Acid distribution Comparison (derived from Table 3)

| Strain | Relevant genotype | Time | Fatty acid distribution (% of total free fatty acid) | | | | % increase C14 | % increase in % C14 |
|---|---|---|---|---|---|---|---|---|
| | | | C14 | C16 | C16:1 | C18 | | |
| WLK310-18 | ΔfadD, ΔpntAB, rcTE+ G2+ | | 0.169 | 0.260 | 0.450 | 0.121 | | |
| WLK310-18G2 | ΔfadD, ΔpntAB, rcTE+ G2+ | | 0.339 | 0.158 | 0.463 | 0.040 | 164.81 | 100.97 | rcTE+: overexpression of acyl-ACP thioesterase from *Ricinus communis*;
G1+: overexpression of a NAD+ dependent 3-oxoacyl-ACP reductase from *M. tuberculosis*
G2+: overexpression of a derivative of a NAD+ dependent 3-oxoacyl-ACP reductase from *M. tuberculosis*
ΔpntAB = deactivation of the membrane bounded transhydrogenase
Δsth = deactivation of the soluble transhydrogenase Again, both NAD+ dependent 3-oxoacyl-ACP reductase carrying strains, WLK309-18G2 and WLK310-18G2, produced significantly more fatty acids and with higher yields than that of the corresponding control strains WLK309-18 and WLK310-18 (Table 3). At 72h, both NAD+ dependent 3-oxoacyl-ACP reductase carrying strains, WLK309-18G2 and WLK310-18G2, produced 13% and 30% more fatty acids with 26% and 30% higher yield than that of the corresponding control strains WLK309-18 and WLK310-18, respectively (Table 3). In addition, both NAD+ dependent 3-oxoacyl-ACP reductase carrying strains, WLK309-18G2 and WLK310-18G2, produced more C14 fatty acids, 73% and 164%, than that of the corresponding control strains, respectively at 72 h (Table 4).

Therefore, these results demonstrate that NADPH is a limiting factor, and it can be alleviated by the introduction of a NAD-dependent 3-oxoacyl-ACP reductase. In addition, the introduction of a NAD-dependent 3-oxoacyl-ACP reductase changes the composition of the fatty acids produced, yielding more C14 chain length fatty acid.

The native NADPH-dependant 3-oxoacyl-ACP reductase was believed to be an essential gene. Therefore, we first tried to reduce its expression with antisense, so that some amount of gene/enzyme activity would remain.

We made expression plasmids encoding 150, 300 and 450 bp antisense against the gene of NADPH-dependant 3-oxoacyl-ACP reductase under the control of an IPTG inducible promoter (lacZ). We measured fatty acid levels at 24 and 48 hrs. See Table 5 and 6.

Surprisingly, those bacteria with reduced native NADPH-dependant 3-oxoacyl-ACP reductase and added NADH-dependant 3-oxoacyl-ACP reductase made more fatty acids that those with wild type levels of expression of NADPH-dependant 3-oxoacyl-ACP reductase and added NADH-dependant 3-oxoacyl-ACP reductase.

TABLE 5

Effect of overexpression NAD+ dependent 3-oxoacyl-ACP reductase from *M. tuberculosis* and inhibition expressing of host FabG using normal design of anti-sense.

| Strains | Relevant genotype | IPTG (mM) | Time | Concentration of fatty acid | | | | | Yield (g fatty acid/ g glucose) | FFA % improvement | Yield % improvement |
|---|---|---|---|---|---|---|---|---|---|---|---|
| | | | | C14 | C16:1 | C16 | C18 | Total | | | |
| ML103 (pWL1TG2) Control | ΔfadD, rcTE+ G2+ | 1 | 24 h | 1.548 | 0.541 | 0.935 | 0.118 | 3.142 | 0.218 | — | — |
| ML103 (pWL1TG2AS1) | ΔfadD, rcTE+ G2+ AS1+ | 0 | | 1.786 | 0.490 | 0.898 | 0.099 | 3.273 | 0.221 | 4.16 | 1.14 |
| ML103 (pWL1TG2AS2) | ΔfadD, rcTE+ G2+ AS2+ | 0 | | 0.831 | 0.770 | 0.442 | 0.134 | 2.178 | 0.158 | −30.70 | −27.56 |
| ML103 (pWL1TG2AS3) | ΔfadD, rcTE+ G2+ AS3+ | 0 | | 0.925 | 0.837 | 0.472 | 0.146 | 2.379 | 0.181 | −24.28 | −16.92 |
| ML103 (pWL1TG2AS1) | ΔfadD, rcTE+ G2+ AS1+ | 1 | | 1.712 | 0.471 | 0.866 | 0.103 | 3.152 | 0.238 | 0.32 | 8.86 |
| ML103 (pWL1TG2AS2) | ΔfadD, rcTE+ G2+ AS2+ | 1 | | 1.077 | 0.981 | 0.476 | 0.150 | 2.684 | 0.193 | −14.58 | −11.38 |
| ML103 (pWL1TG2AS3) | ΔfadD, rcTE+ G2+ AS3+ | 1 | | 1.031 | 0.870 | 0.439 | 0.134 | 2.474 | 0.171 | −21.25 | −21.83 |
| ML103 (pWL1TG2) Control | ΔfadD, rcTE+ G2+ | 1 | 48 h | 1.640 | 0.580 | 1.005 | 0.127 | 3.352 | 0.217 | — | — |
| ML103 (pWL1TG2AS1) | ΔfadD, rcTE+ G2+ AS1+ | 0 | | 2.122 | 0.569 | 1.065 | 0.116 | 3.872 | 0.257 | 15.52 | 18.81 |
| ML103 (pWL1TG2AS2) | ΔfadD, rcTE+ G2+ AS2+ | 0 | | 1.218 | 0.994 | 0.796 | 0.182 | 3.190 | 0.217 | −4.84 | 0.00 |
| ML103 (pWL1TG2AS3) | ΔfadD, rcTE+ G2+ AS3+ | 0 | | 1.215 | 1.117 | 0.595 | 0.186 | 3.113 | 0.207 | −7.12 | −4.31 |
| ML103 (pWL1TG2AS1) | ΔfadD, rcTE+ G2+ AS1+ | 1 | | 2.167 | 0.566 | 1.053 | 0.122 | 3.907 | 0.270 | 16.55 | 24.43 |
| ML103 | ΔfadD, rcTE+ | 1 | | 1.305 | 1.209 | 0.598 | 0.196 | 3.308 | 0.232 | −1.33 | 6.94 |

TABLE 5-continued

Effect of overexpression NAD+ dependent 3-oxoacyl-ACP reductase from *M. tuberculosis* and inhibition expressing of host FabG using normal design of anti-sense.

| Strains | Relevant genotype | IPTG (mM) | Time | C14 | C16:1 | C16 | C18 | Total | Yield (g fatty acid/ g glucose) | FFA % improvement | Yield % improvement |
|---|---|---|---|---|---|---|---|---|---|---|---|
| (pWL1TG2AS2) | G2+ AS2+ | | | | | | | | | | |
| ML103 (pWL1TG2AS3) | ΔfadD, rcTE+ G2+ AS3+ | 1 | | 1.328 | 1.144 | 0.557 | 0.176 | 3.204 | 0.210 | −4.41 | −2.89 | rcTE+: overexpression of acyl-ACP thioesterase from *Ricinus communis*;
G2+: overexpression of a derivative of a NAD+ dependent 3-oxoacyl-ACP reductase from *M. tuberculosis*
AS1+~AS3+: anti-sense fabG targeting the *E. coli* fabG structural gene with different lengths of 400, 250 and 150, respectively

TABLE 6

Fatty Acid distribution Comparison (derived from Table 5)

| Strains | Relevant genotype | IPTG (mM) | Time | C14 | C16:1 | C16 | C18 | % increase C14 | % increase in % C14 |
|---|---|---|---|---|---|---|---|---|---|
| ML103 (pWL1TG2) Control | ΔfadD, rcTE+ G2+ | 1 | 24 h | 49.25 | 17.22 | 29.76 | 3.77 | — | — |
| ML103 (pWL1TG2AS1) | ΔfadD, rcTE+ G2+ AS1+ | 0 | | 54.58 | 14.97 | 27.42 | 3.03 | 15.43 | 10.81 |
| ML103 (pWL1TG2AS2) | ΔfadD, rcTE+ G2+ AS2+ | 0 | | 38.18 | 35.37 | 20.28 | 6.17 | −46.28 | −22.47 |
| ML103 (pWL1TG2AS3) | ΔfadD, rcTE+ G2+ AS3+ | 0 | | 38.87 | 35.18 | 19.82 | 6.13 | −40.24 | −21.08 |
| ML103 (pWL1TG2AS1) | ΔfadD, rcTE+ G2+ AS1+ | 1 | | 54.32 | 14.93 | 27.49 | 3.26 | 10.65 | 10.30 |
| ML103 (pWL1TG2AS2) | ΔfadD, rcTE+ G2+ AS2+ | 1 | | 40.12 | 36.54 | 17.75 | 5.59 | −30.41 | −18.53 |
| ML103 (pWL1TG2AS3) | ΔfadD, rcTE+ G2+ AS3+ | 1 | | 41.65 | 35.17 | 17.75 | 5.43 | −33.40 | −15.42 |
| ML103 (pWL1TG2) Control | ΔfadD, rcTE+ G2+ | 1 | 48 h | 48.93 | 17.31 | 29.97 | 3.79 | — | — |
| ML103 (pWL1TG2AS1) | ΔfadD, rcTE+ G2+ AS1+ | 0 | | 54.80 | 14.71 | 27.49 | 3.00 | 29.39 | 12.01 |
| ML103 (pWL1TG2AS2) | ΔfadD, rcTE+ G2+ AS2+ | 0 | | 38.19 | 31.17 | 24.95 | 5.69 | −25.73 | −21.95 |
| ML103 (pWL1TG2AS3) | ΔfadD, rcTE+ G2+ AS3+ | 0 | | 39.03 | 35.86 | 19.12 | 5.99 | −25.91 | −20.23 |
| ML103 (pWL1TG2AS1) | ΔfadD, rcTE+ G2+ AS1+ | 1 | | 55.46 | 14.48 | 26.94 | 3.12 | 32.10 | 13.34 |
| ML103 (pWL1TG2AS2) | ΔfadD, rcTE+ G2+ AS2+ | 1 | | 39.44 | 36.55 | 18.07 | 5.94 | −20.46 | −19.39 |
| ML103 (pWL1TG2AS3) | ΔfadD, rcTE+ G2+ AS3+ | 1 | | 41.44 | 35.71 | 17.37 | 5.48 | −19.03 | −15.30 | rcTE+: overexpression of acyl-ACP thioesterase from *Ricinus communis*;
G2+: overexpression of a derivative of a NAD+ dependent 3-oxoacyl-ACP reductase from *M. tuberculosis*
AS1+~AS3+: anti-sense fabG targeting the *E. coli* fabG structural gene with different lengths of 400, 250 and 150, respectively We also knocked out the native NADPH-dependant 3-oxoacyl-ACP reductase and added NADH-dependant 3-oxoacyl-ACP reductase, but these cells did less well that those cells with wild type NADPH-dependant 3-oxoacyl-ACP reductase and added NADH-dependent 3-oxoacyl-ACP reductase (data not shown) possibly because the expression level of the added gene was not high enough. However, we expect that further fine-tuning of the NADH-dependent 3-oxoacyl-ACP reductase will improve the fatty acid production, and experiments are in progress to show this.

We expect that combining the introduction of NADH-dependent 3-oxoacyl-ACP reductase with overexpressed UDH+ and/or PntAB+ will improve the fatty acid production because it will allow efficient usage of both NADH-dependent 3-oxoacyl-ACP reductase and the native NADPH-dependent 3-oxoacyl-ACP reductase, and experiments are in progress to show this.

Our lab has made many engineered bacteria that produced increased amount of fatty acids, and many of those modifications are compatible herewith. Direct strategies that have been tested and proven effective can be classified into two broad categories: i) overexpression of enzymes catalyzing key steps in the fatty acid synthesis pathway, including endogenous or heterologous thioesterases (TE), acetyl-CoA carboxylase (ACC), and acyl-CoA ligases (ACL); and ii) deletion of enzymes involved in the β-oxidation pathway that degrades fatty acids, such as acyl-CoA dehydrogenase (FadE), acyl-CoA synthetase (FadD), and a long-chain fatty acid outer membrane transporter (FadL). In one of the latest studies, efforts along this direction led to a titer of 5.1 g/L extracellular fatty acids and a yield of 4.1% (g per g glucose supplied) in a fed-batch culture with online product extraction.

The research efforts described above focused on local pathways directly related to fatty acids. However, modifications in distant pathways, such as glycolysis or TCA cycle, can also improve fatty acid synthesis through redistribution of metabolite precursors towards fatty acid production.

For example, the level of malonyl-CoA, a precursor for fatty acids was improved 15-fold through the deletion of ackA-pta and adhE, together with the overexpression of acetyl-CoA synthetase (Acs).

For another example, there are two other lactate dehydrogenases in *E. coli* encoded by ldhA and lldD. Knocking one or both out would block the formation of lactate from pyruvate and direct more carbon towards fatty acid biosynthesis.

Second, there is another acetate-producing pathway catalyzed by poxB encoded pyruvate oxidase. Even though the amount of acetate was quite low after pta was deleted in the above study, further knockout of poxB would lead to complete elimination of this by-product.

Finally, it has been suggested that derepression of the glyoxylate bypass by iclR deletion alone cannot draw isocitrate from the TCA cycle to the glyoxylate bypass because enzyme IcdA has a stronger affinity to isocitrate than enzymes AceA and AceB. Hence, to fully activate the glyoxylate bypass, icdA may need to be knocked out in addition to iclR.

These genetic combinations with the invention described herein will be explored in our future study, and the work is expected to proceed quickly as many base strains and/or expression plasmids are already available.

High fat producing microbes can also be combined with genes that would allow the microbes to use less energy intensive food sources than glucose. For example, glycerol is a by-product of biodiesel production and is a very inexpensive food-source, and microbes can be altered to allow growth on glycerol. See Murarka (2008). As another example, cellulosic food-sources are also readily available, and microbes have been engineered to secrete cellulose degrading enzymes and thus are able to grow or e.g., switchgrass. Bokinsky (2011). Ultimately, the engineered microbes described herein may be combined with this additional type of engineering as the microbes are adapted for large scale production of fats or their derivatives.

We predict that the inventive concept can be applied to other organisms having Type II fatty acid synthesis systems to achieve similar improvement of fatty acid production, as long as suitable $NAD^+$-dependent 3-oxoacyl-ACP reductase, native or engineered or exogenous, is available to replace or augment the native $NADP^+$-dependent 3-oxoacyl-ACP reductase.

As shown herein, there are thousands of such enzyme sequences that can be used when placed into a suitable expression vector for the chosen host species. If expression levels are low, the codon usage can be optimized for the species in question, as optimized codon charts are available for many species. Further, the genes are fairly small, and complete synthesis of an optimized codon ORF would be fairly quick and inexpensive.

We expect that the higher availability of $NAD^+$ than $NADP^+$ in such organisms will make the concept equally beneficial in these FASII organisms. Examples of FASII organisms include most bacteria, algae and plants, including but not limited to *Escherichia, Bacillus, Lactobacillus, Staphylococcus, Salmonella, Haemophilus, Lemnoideae, Chlamydomonas, Chlorella, Nannochloropsis*. Yeast mitochondria have FASII genes, as well. Future experiments may test one of the microalgae or other bacteria, and we expect that improved production will be found on replacing or supplementing NADP-based enzymes with NADH-based enzymes.

The above experiments can be repeated in *Bacillus subtilis*. The same genes can be used, especially since *Bacillus* has no significant codon bias. A protease-deficient strain like WB800N is preferably used for greater stability of heterologous protein. The *E. coli-B. subtilis* shuttle vector pMTLBS72 exhibiting full structural stability can be used to move the genes easily to a more suitable vector for *Bacillus*. Alternatively, two vectors pHT01 and pHT43 allow high-level expression of recombinant proteins within the cytoplasm. As yet another alternative, plasmids using the theta-mode of replication such as those derived from the natural plasmids pAMβ1 and pBS72 can be used. Several other suitable expression systems are available. Since the FAS genes are ubiquitous, the invention is predicted to function in *bacillus*.

Figure 1A:
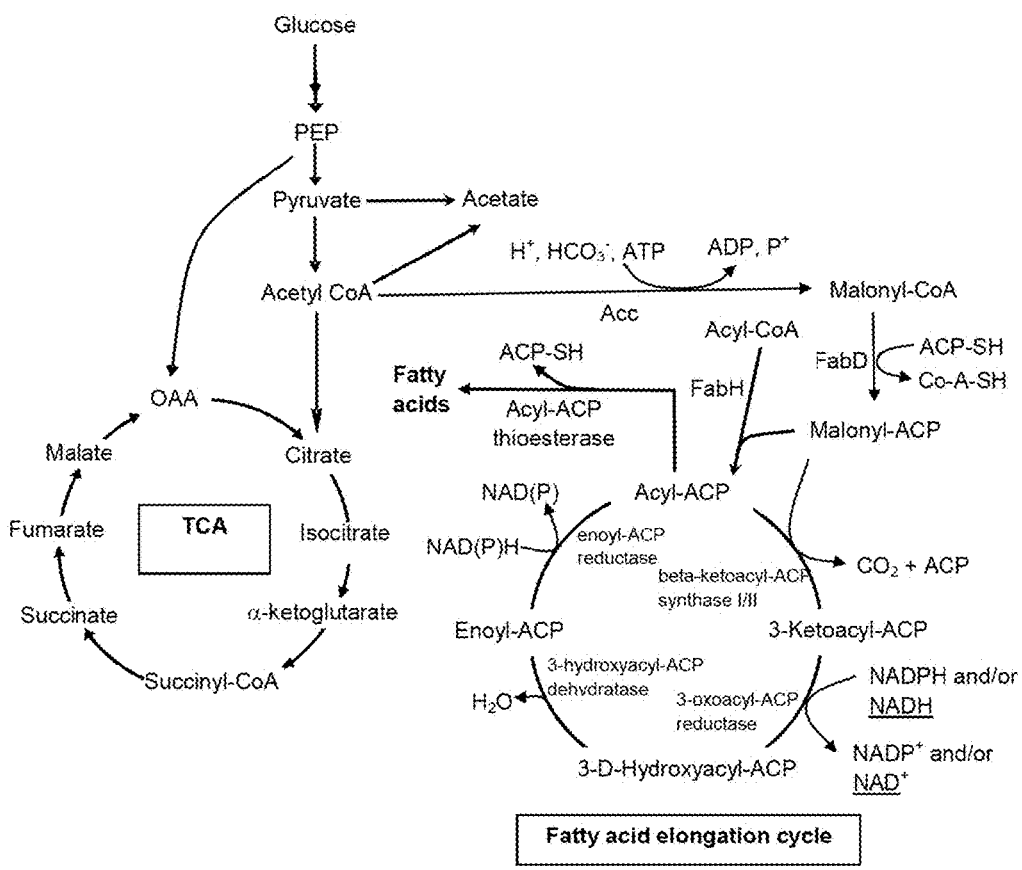
FIG. 1A is a simplified diagram of central aerobic metabolic pathway and the fatty acid synthesis pathway of E. coli, including the newly added NAD$^+$-dependent 3-oxoacyl-[acyl-carrier-protein] (ACP) reductase (underlined).
Figure 1B:
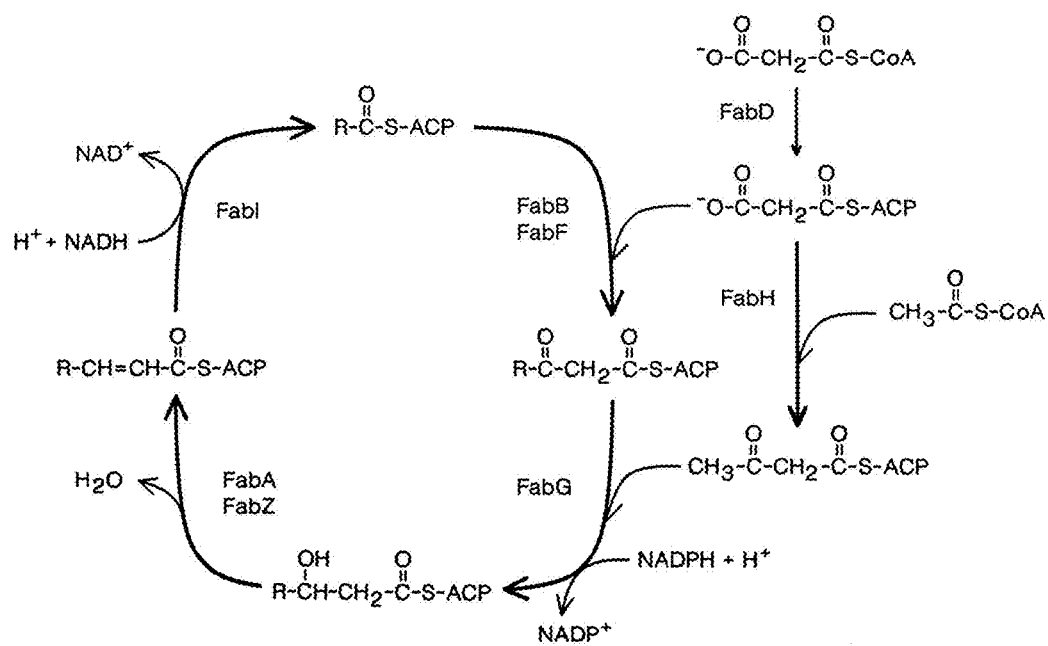
FIG. 1B is a simplified diagram of typical fatty acid synthesis pathway of E. coli.

The inventors further tested the effect of co-overexpressing mtFabG (FabG gene obtained from *Mycobacterium tuberculosis*) and FabZ in order to improve fatty acid productivity. This is prompted by the observation of the following experiment with higher overexpression of mt FabG2 (3-ketoacyl-ACP reductase obtained from *Mycobacterium tuberculosis*). FabZ is 3R-hydroxymyristoyl ACP dehydratase, and as shown in FIG. 1B, it is involved in fatty acid synthesis.

Figure 3B:
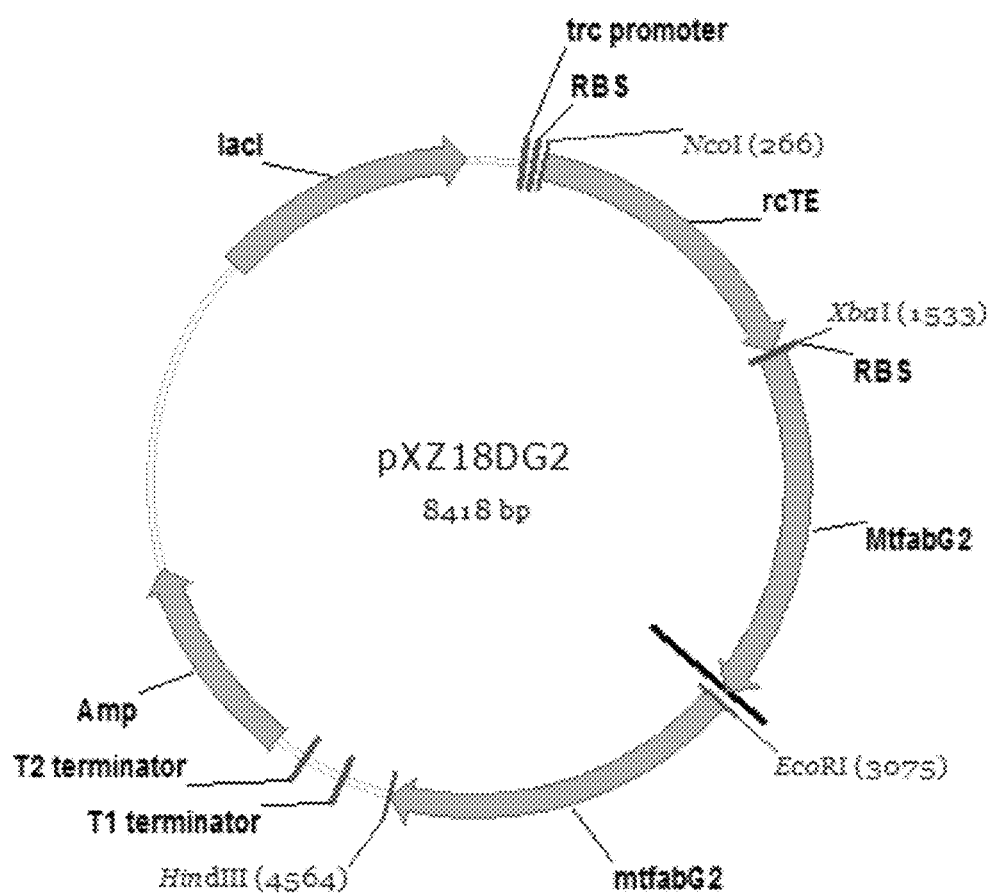
FIG. 3B is a schematic diagram of the plasmid construct pXZ18DG2 which is derived from the plasmid pXZ18G2 by adding an additional copy of mtG2. Similar to pXZ18G2, the plasmid also carries an acyl-ACP thioesterase from *Ricinus communis* (accession number: XM002515518) (Zhang et al., 2011) and a NAD+ dependent 3-oxoacyl-ACP reductase from *Mycobacterium tuberculosis* (accession number: Rv0242c). Abbreviations: RBS, ribosomal binding site; rcTE, acyl-ACP thioesterase from *R. communis*; mtG2, a NAD+ dependent 3-oxoacyl-ACP reductase from *M. tuberculosis* with an omission of the first 16 amino acids; lacI, regulator gene of trc promoter system; AmpR, ampicillin resistant gene; T1 terminator and T2 terminator, transcriptional terminator of rrnB; pBR322 origin, origin of replication.
Figure 8A:
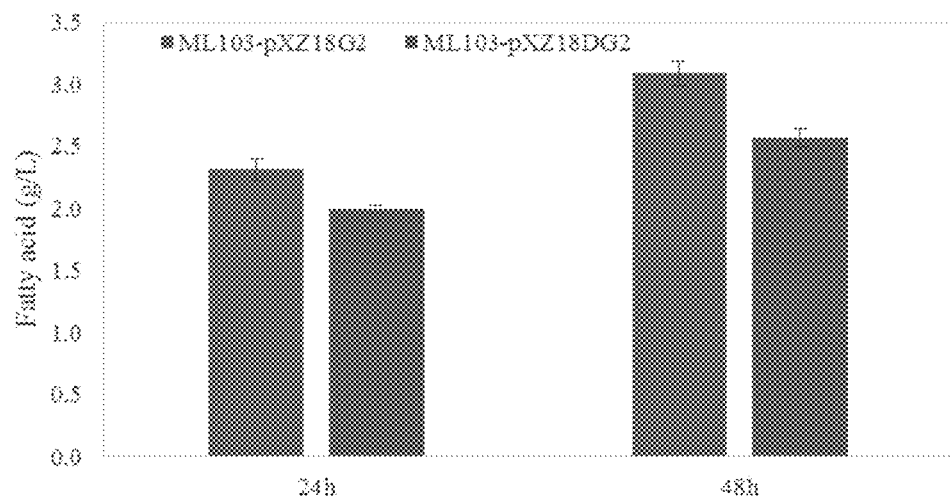
FIG. 8A-B: Effect of higher expression of mt FabG2 on fatty acid production. Plasmid pWL1Tg2 carries an acyl-ACP thioesterase and truncated fabG from *Mycobacterium tuberculosis* under a constitutive promoter system. Plasmid pXZ18DG2 carries an acyl-ACP thioesterase and two copies of truncated fabGs from *Mycobacterium tuberculosis* under an inducible trc promoter system.
Figure 8B:
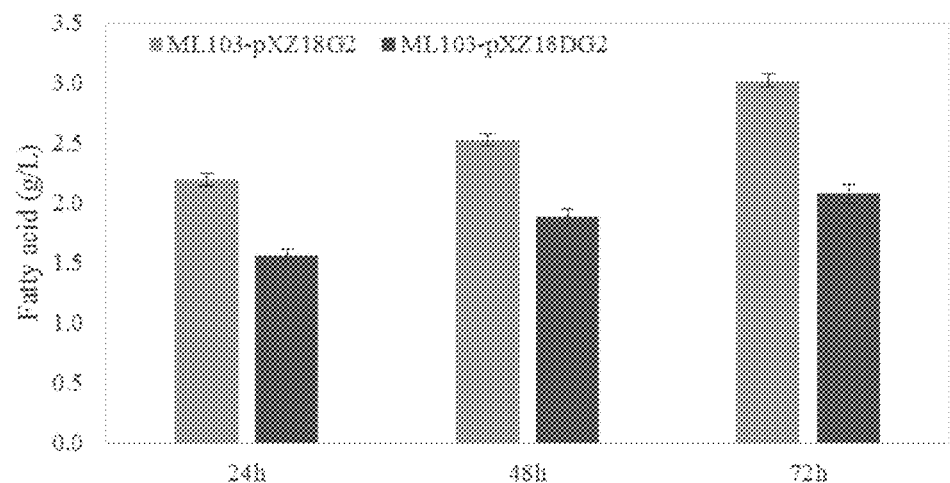

An experiment was designed to test if the expression of mt FabG is the limiting factor by cloning two copies of the mt fabG genes in the same plasmid (the resulting plasmid is called pXZ18DG2, as shown in FIG. 3B). Fermentation experiments were performed with ML103 as the host carrying either the plasmid pXZ18G2 or pXZ18DG2 in glucose or glycerol supplemented LB medium. The results are shown in FIG. 8A-B. The values shown are the average of triplicate runs. Unlike previous experimental observations that overexpression of a single copy of mt fabG gene increases fatty acid production, the double mt FabG did not show any improvement when comparing the strain ML103 (pXZ18G2) with ML103(pXZ18DG2) in both glucose and glycerol. The decrease in fatty acid titer is more significant in glycerol than that of glucose. This reduction of fatty acid production in strains carrying pXZ18DG2 suggests that too much β-ketoacyl reductase activity or NADH supply would lead to discoordination within the fatty acid elongation cycle. We hypothesize that increased β-ketoacyl reductase activity resulted in an accumulation of 3-hydroxyacyl-ACP and thus might cause feedback inhibition. It has been reported that acyl-ACP intermediates might act as feedback inhibitors for fatty acid production.

Figure 9:
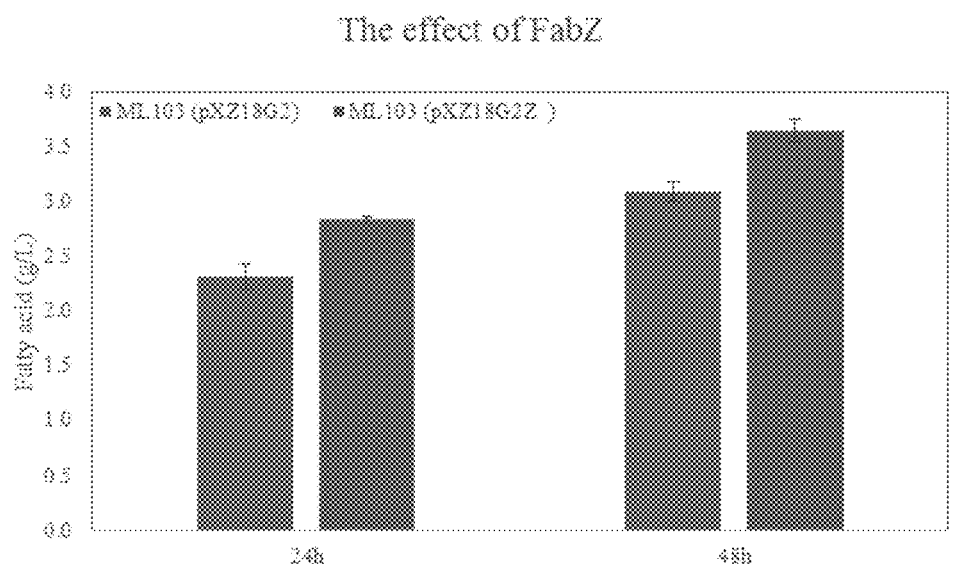
FIG. 9: Effect of co-overexpression of mt FabG2a and ec FabZ on fatty acid production. Plasmid pWL1TG2 carries an acyl-ACP thioesterase and truncated fabG from *Mycobacterium tuberculosis* under a constitutive promoter system. Plasmid pWL1TG2Z carries an acyl-ACP thioesterase, truncated fabG from *Mycobacterium tuberculosis* and fabZ gene from *E. coli* under an inducible trc promoter system.

The inventors further tested the hypothesis of recovering the coordination among the reactions within the fatty acid elongation cycle by co-overexpressing mt FabG and FabZ in order to improve fatty acid productivity. The results shown in FIG. 9 support the hypothesis that FabG might not be the only limiting factor. The fatty acid production by the mt FabG and FabZ double-overexpression strain increased by about 20% when compared to the strain with mt FabG overexpression alone. Co-overexpression of FabZ, downstream of mt FabG, alleviates the imbalance caused by the overexpression of mt FabG alone, leading to an improved performance.

The inventors also examined the effect of down regulation of the native *E. coli* NADPH-dependent FabG (ec FabG) on fatty acid production. Since NADH is more readily available in *E. coli* and that the NADH-dependent FabG (mt FabG) should be more efficient than the native ec FabG, we speculate that fatty acid production can be improved by increasing the relative ratio of the newly introduced mt FabG to that of the native ec FabG. We chose to use the anti-sense RNA techniques to decrease the expression of ec fabG since fabG is an essential gene.

Figure 10:
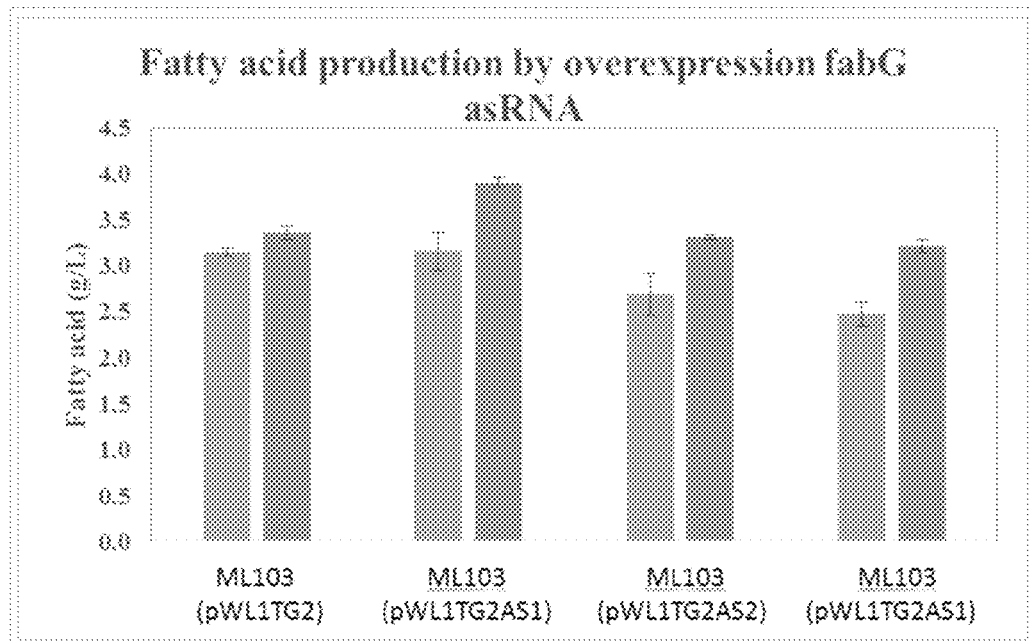
FIG. 10: Effect of antisense ec fabG on fatty acid production. Plasmid pWL1TG2 carries an acyl-ACP thioesterase and truncated fabG from *Mycobacterium tuberculosis* under a constitutive promoter system. Plasmids pWL1TG2AS, pWL1TG2AS2 and pWL1TG2AS3 are derived from plasmid pWL1TG2 with additional anti-sense RNAs of ec fabG of different length. The number 1 to 3 denotes the length of the anti-sense of 450, 300 and 150 bp, respectively.

The fermentation data showed that only the strain carry the plasmid with the longest anti-sense RNA, pWL1TG2AS1, produced similar amount of fatty acid as control strain at 24 h, the other two strains carrying plasmids pWL1TG2AS2 or pWL1TG2AS3 were significantly lower (FIG. 10). These two strains however caught up at 48 h, but the final total fatty acid concentrations were similar to that of the control. At 48 h, the strain carrying pWL1TG2AS1 produced about 3.9 g/L fatty acid, which is 16.5% higher than that of the control. Bacterial RNAs are typically short lived, and some of the reports suggested that half-life is an important factor in anti-sense RNA efficiency. It is therefore possible that the shorter sequences are more likely to be degraded quicker. As a result, only the longest anti-sense RNA showed the positive improvement effect. The results also indicated that a system with mt FabG overexpression and native FabG down regulation provides the best performance.

In order to better compare the effect of down-regulating the native ec fabG, a paired-termini (PT) design was used to stabilize the anti-sense RNA. All three newly paired termini anti-sense RNA constructs (pHWTAS1, pHWTAS2, pHW-TAS3) shared the same length and sequence as the earlier design, except being stabilized by the addition of a hairpin structure. A control plasmid pHWTASC was also constructed using a dummy sequence to replace the anti-sense portion.

Figure 11:
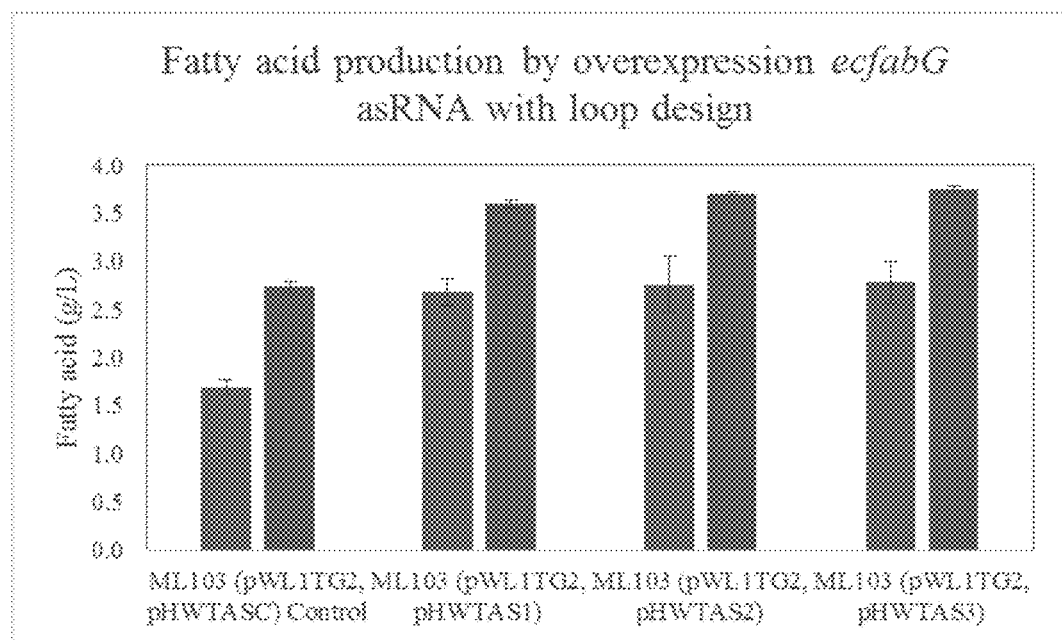
FIG. 11: Effect of antisense ec fabG on fatty acid production. Plasmid pWL1TG2 carries an acyl-ACP thioesterase and truncated fabG from *Mycobacterium tuberculosis* under a constitutive promoter system; plasmids pHWTAS1, pHWTAS2, pHWTAS3 is pBAD33 based which carries an acyl-ACP thioesterase under a constitutive promoter and different length of anti-sense RNAs of ec fabG with a loop design as a stabilizer under an inducible trc promoter. The number 1 to 3 denotes the length of the anti-sense of 450, 300 and 150 bp, respectively.

FIG. 11 shows the effect of anti-sense RNAs expression, all three strains carrying the new anti-sense constructs showed similar improved fatty acid production over the control strain. The final titers are 3.59, 3.72 and 3.76 g/L compared to the control of 2.74 g/L, which represent improvements of 31.1%, 35.2% and 36.8%, respectively. The results further indicate that overexpression of a NAD-dependent mt FabG and down-regulating the native NADPH-dependent ecFabG is a practical approach to improve fatty acid production in *E. coli*.

Although work is still needed to scale up microalgae production for use in making biofuels, they are especially attractive as a source of fuel from an environmental standpoint because they consume carbon dioxide and can be grown on marginal land, using waste or salt water.

Indeed, Ann Ruffings group from Sandia National Laboratories has already engineered two strains of cyanobacteria to produce free fatty acid, and is working with a third. The cyanobacteria were chosen because fuel from engineered cyanobacteria is excreted outside the cell, in contrast to eukaryotic algae, in which fuel production occurs inside the cell. This greatly simplifies scale up, as the cyanobacteria continue to grow, while fats are skimmed from the top of the culture media.

In addition, Radakovitz has overexpressed two genes encoding acyl-ACP thioesterase (TE) of plant origin in *P. tricornutum* to produce medium-chain fatty acids in the oil fraction. These results provide adequate foundation for applying this invention to microalgae, such that the NADPH dependent 3-oxoacyl-ACP reductase is supplemented or replaced with an NADH-dependent enzyme.

Further, significant advances in microalgal genomics have been achieved during the last decade. Expressed sequence tag (EST) databases have been established; nuclear, mitochondrial, and chloroplast genomes from several microalgae have been sequenced; and several more are being sequenced. Historically, the green alga *Chlamydomonas reinhardtii* has been the focus of most molecular and genetic physiological research. Therefore, most of the tools for the expression of transgenes and gene knockdown have been developed for and are specific for this species. However, tools are now also being rapidly developed for diatoms and other algae that are of greater interest for industrial applications.

Additionally, successful genetic transformation has been reported for the green (Chlorophyta), red (Rhodophyta), and brown (Phaeophyta) algae; diatoms; euglenids; and dinoflagellates, although the efficiency of transformation seems to be strongly species dependent, and the method of transformation has to be carefully selected and optimized for each microalga, and the stability of expression improved through proper codon usage, the use of strong endogenous promoters, and inclusion of species-specific 5', 3', and intron sequences.

The following references are incorporated by reference in their entirety for all purposes.

All accession numbers referenced herein, and the sequences and data therein, are incorporated by reference herein in their entireties for all purposes. Accession numbers can be accessed, e.g., at GenBank, EMBL, Brenda, UniProt and the like.

Bergler H, et a., Protein EnvM is the NADH-dependent enoyl-ACP reductase (FabI) of *Escherichia coli*, J Biol Chem. 269(8):5493-6 (1994).

Bokinsky G. et al., Synthesis of three advanced biofuels from ionic liquid-pretreated switchgrass using engineered *Escherichia coli*, PNAS, 108(50): 19949-19954 (2011).

Caughey I, Kekwick R G, The characteristics of some components of the fatty acid synthetase system in the plastids from the mesocarp of avocado (*Persea americana*) fruit, Eur J Biochem. 123(3):553-61 (1982).

Dutta D, et al., Crystal structure of FabG4 from *Mycobacterium tuberculosis* reveals the importance of C-terminal residues in ketoreductase activity, J Struct Biol. 174(1): 147-55 (2011).

Fuhrer T, Sauer U. Different biochemical mechanisms ensure network-wide balancing of reducing equivalents in microbial metabolism, J Bacteriol. 191(7):2112-21 (2009).

Jing et al., Phylogenetic and experimental characterization of an acyl-ACP thioesterase family reveals significant diversity in enzymatic specificity and activity, BMC Biochemistry 2011, 12:44.

Martínez I, et al., Replacing *Escherichia coli* NAD-dependent glyceraldehyde 3-phosphate dehydrogenase (GAPDH) with a NADP-dependent enzyme from *Clostridium acetobutylicum* facilitates NADPH dependent pathways, Metab Eng. 10(6):352-9 (2008).

Murarka A., et al., Fermentative Utilization of Glycerol by *Escherichia coli* and Its Implications for the Production of Fuels and Chemicals, Appl Environ Microbiol. February 2008; 74(4): 1124-1135.

Radakovits, R., Eduafo, P. M. and Posewitz, M. C. Genetic engineering of fatty acid chain length in *Phaeodactylum tricornutum*. Metab. Engin., 13, 89-95 (2011).

Ruffing, A. M. & Jones, H. D. T. Physiological effects of free fatty acid production in genetically engineered *Synechococcus elongatus* PCC 7942. *Biotechnology and Bioengineering*, 2012; 109 (9): 2190.

Sanchez A M, et al., Effect of overexpression of a soluble pyridine nucleotide transhydrogenase (UdhA) on the production of poly(3-hydroxybutyrate) in *Escherichia coli*, Biotechnol Prog. 22(2):420-5 (2006).

Wang Y, at al, Improvement of NADPH bioavailability in *Escherichia coli* by replacing NAD+-dependent glyceraldehyde-3-phosphate dehydrogenase GapA with NADP+-dependent GapB from *Bacillus subtilis* and addition of NAD kinase, J Ind Microbiol Biotechnol. 2013. PMID: 24048943.

Zhang X, Li M, Agrawal A, San K Y, Efficient free fatty acid production in *Escherichia coli* using plant acyl-ACP thioesterases, Metab Eng. 13(6):713-22 (2011).

WO2013096665 Long chain organic acid bioproduction.
WO2011064183 Novel fatty acid elongase and uses thereof
WO2010142522 Novel fatty acid elongation components and uses thereof
WO2012052468 Novel fatty acid desaturases, elongases, elongation components and uses thereof
US20140093921, WO2011116279 Bacteria and method for synthesizing fatty acids
WO2013059218 Bacteria and method for synthesizing fatty acids
US20140212935 Short chain fatty acids from bacteria
US20140193867 Microbial odd chain fatty acids

---

What is claimed is:

1. An engineered FASII bacteria with improved productivity of a fatty acid or fatty acid derivative, said FASII bacteria comprising type II fatty acid synthesis enzymes (FASII) and
    a) an overexpressed NAD+-dependent 3-oxoacyl-ACP reductase or an overexpressed NAD$^+$-dependent 3-oxoacyl-CoA reductase that replaces or supplements a native NADP$^+$-dependent 3-oxoacyl-ACP reductase or 3-oxoacyl-CoA reductase (respectively);
    and b) one or more overexpressed acyl-ACP thioesterases (TE)
    wherein said NAD+-dependent 3-oxoacyl-ACP reductase has the amino acid sequence of SEQ ID NO. 2.

2. The engineered microbe of claim 1, said FASII bacteria further comprising reduced activity of one or more enzymes selected from beta-oxidation cycle enzymes, acetate synthesis enzymes, lactate synthesis enzymes, formate synthesis enzymes, ethanol synthesis enzymes, glycolytic enzymes or tricarboxylic acid (TCA) cycle enzymes.

3. The engineered FASII bacteria of claim 1, wherein said NAD+-dependent 3-oxoacyl-ACP reductase or NAD$^+$-dependent 3-oxoacyl-CoA reductase is from *Mycobacterium tuberculosis*.

4. The engineered FASII bacteria of claim 1, said engineered FASII bacteria further comprising at least one downregulated or disrupted gene selected from one or more of fadD, fabG, sth and pntAB.

5. The engineered FASII bacteria of claim 4, wherein the downregulated or disrupted gene is achieved by using antisense RNA (asRNA).

6. The engineered FASII bacteria of claim 1, wherein i) at least one protein from the tricarboxylic acid cycle is reduced, or ii) at least one protein from glycolysis is reduced, or both i) and ii) are reduced.

7. A method of making fatty acids, comprising growing engineered FASII bacteria of claim 1 in a nutrient broth for a time sufficient to make fatty acids, and isolating said fatty acids.

* * * * *